United States Patent
Yim et al.

(10) Patent No.: US 11,660,129 B2
(45) Date of Patent: May 30, 2023

(54) TIGHTENING DEVICE FOR SPINE SURGERY

(71) Applicant: DePuy Synthes Products, Inc., Raynham, MA (US)

(72) Inventors: Jason Yim, San Francisco, CA (US); Dennis Chien, West Chester, PA (US); Barclay Davis, Glenmoore, PA (US); David Rathbun, Gap, PA (US); Josef Gabelberger, West Chester, PA (US); Zoher S. Bootwala, Wimington, DE (US); Scott Larsen, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 200 days.

(21) Appl. No.: 15/788,149

(22) Filed: Oct. 19, 2017

(65) Prior Publication Data

US 2018/0036046 A1   Feb. 8, 2018

Related U.S. Application Data

(62) Division of application No. 12/901,473, filed on Oct. 8, 2010, now abandoned.

(60) Provisional application No. 61/278,671, filed on Oct. 9, 2009.

(51) Int. Cl.
*A61B 17/70* (2006.01)

(52) U.S. Cl.
CPC ...... *A61B 17/7091* (2013.01); *A61B 17/7032* (2013.01); *A61B 17/7076* (2013.01)

(58) Field of Classification Search
CPC ............ A61B 17/7091; A61B 17/7074; A61B 17/7082
See application file for complete search history.

(56) References Cited

U.S. PATENT DOCUMENTS

| | | | |
|---|---|---|---|
| 5,520,689 A | 5/1996 | Schläpfer et al. | |
| 6,299,616 B1 * | 10/2001 | Beger | A61B 17/7044 606/86 A |
| 6,723,100 B2 | 4/2004 | Biedermann et al. | |
| 7,266,500 B2 | 9/2007 | Schramm | |
| 7,278,995 B2 * | 10/2007 | Nichols | A61B 17/7032 606/272 |

(Continued)

*Primary Examiner* — Lynnsy M Summitt
(74) *Attorney, Agent, or Firm* — Meunier Carlin & Curfman LLC

(57) ABSTRACT

A device for spinal surgery that may be used for tightening a locking cap onto at least a portion of a pedicle screw. The device may include a torque-generating body having a proximal end and an opposing distal end and a drive shaft rotatably driven by the torque-generating body. A proximal end of the drive shaft may be operatively engaged to the distal end of the torque-generating body and an opposing distal end of the drive shaft may engage at least a portion of one of the locking cap and the pedicle screw. An anti-torque device is provided that has an elongated and generally hollow member defining a longitudinal axis. The member has a proximal end and an opposing distal end, where the proximal end of the anti-torque device may be fixed from rotating relative to at least a portion of the torque-generating body and the distal end may be fixed from rotating relative to a spine rod or a pedicle screw.

18 Claims, 18 Drawing Sheets

(56) References Cited

U.S. PATENT DOCUMENTS

| | | | | |
|---|---|---|---|---|
| 7,296,500 B1* | 11/2007 | Martinelli | A61B 17/8875 | 606/308 |
| 7,363,838 B2* | 4/2008 | Abdelgany | A61B 17/8875 | 81/177.1 |
| 7,465,306 B2* | 12/2008 | Pond, Jr. | A61B 17/7079 | 606/104 |
| 7,585,315 B2 | 9/2009 | Donath | | |
| 7,621,918 B2* | 11/2009 | Jackson | A61B 17/7037 | 606/86 A |
| 7,862,587 B2* | 1/2011 | Jackson | A61B 17/861 | 606/246 |
| 7,914,559 B2* | 3/2011 | Carls | A61B 17/7032 | 606/270 |
| 7,985,242 B2* | 7/2011 | Forton | A61B 17/7086 | 606/246 |
| 8,016,832 B2* | 9/2011 | Vonwiller | A61B 17/7032 | 606/86 A |
| 8,066,739 B2* | 11/2011 | Jackson | A61B 17/7008 | 606/246 |
| 8,172,847 B2* | 5/2012 | Dziedzic | A61B 17/7091 | 606/86 A |
| 8,206,394 B2* | 6/2012 | Stad | A61B 17/7091 | 606/86 A |
| 8,308,729 B2* | 11/2012 | Nunley | A61B 17/7086 | 606/86 A |
| 8,317,796 B2* | 11/2012 | Stihl | A61B 17/7091 | 606/279 |
| 8,454,658 B2* | 6/2013 | Lindner | A61B 17/7041 | 606/246 |
| 8,535,318 B2* | 9/2013 | Peterson | A61B 17/0218 | 606/86 A |
| 8,986,349 B1* | 3/2015 | German | A61B 17/7068 | 606/279 |
| 9,017,333 B2* | 4/2015 | Beale | A61B 17/92 | 606/80 |
| 9,050,148 B2* | 6/2015 | Jackson | A61B 17/7038 | |
| 9,149,308 B2* | 10/2015 | Biedermann | A61B 17/7091 | |
| 9,198,692 B1* | 12/2015 | Doose | A61B 17/7032 | |
| 9,198,698 B1* | 12/2015 | Doose | A61B 17/708 | |
| 9,211,149 B2* | 12/2015 | Hoefer | A61B 17/708 | |
| 9,526,537 B2* | 12/2016 | Meyer | A61B 17/7086 | |
| 9,532,814 B2* | 1/2017 | Harper | A61B 17/7086 | |
| 9,629,667 B2* | 4/2017 | Petit | A61B 17/7076 | |
| 9,744,654 B2* | 8/2017 | Bootwala | A61B 17/7091 | |
| 9,750,548 B2* | 9/2017 | George | A61B 17/7091 | |
| 9,861,419 B2* | 1/2018 | Schafer | A61B 17/8875 | |
| 9,907,582 B1* | 3/2018 | Olea | A61B 17/7079 | |
| 9,980,758 B2* | 5/2018 | Abidin | A61B 17/708 | |
| 10,058,355 B2* | 8/2018 | Beyer | A61B 17/7032 | |
| 2005/0192589 A1 | 9/2005 | Raymond et al. | | |
| 2006/0036244 A1 | 2/2006 | Spitler et al. | | |
| 2008/0015601 A1* | 1/2008 | Castro | A61B 17/7086 | 606/86 R |
| 2008/0154277 A1* | 6/2008 | Machalk | A61B 17/7091 | 606/99 |
| 2008/0154278 A1* | 6/2008 | Abdelgany | A61B 17/8875 | 606/99 |
| 2008/0282846 A1* | 11/2008 | Sharifi-Mehr | B25B 17/02 | 81/57 |
| 2008/0294202 A1 | 11/2008 | Peterson et al. | | |
| 2010/0023019 A1 | 1/2010 | Fuhrer et al. | | |
| 2010/0292742 A1* | 11/2010 | Stad | A61B 17/7091 | 606/86 A |
| 2011/0004222 A1* | 1/2011 | Biedermann | A61B 17/7091 | 606/104 |
| 2011/0066156 A1* | 3/2011 | McGahan | A61B 17/7091 | 606/99 |
| 2014/0277203 A1* | 9/2014 | Atoulikian | A61B 17/7091 | 606/86 A |
| 2015/0105831 A1* | 4/2015 | Yim | A61B 17/7091 | 606/86 A |
| 2017/0079696 A1* | 3/2017 | Walker | A61B 17/708 | |
| 2018/0070987 A1* | 3/2018 | Su | A61B 17/001 | |
| 2018/0177536 A1* | 6/2018 | Divincenzo | A61B 17/7082 | |
| 2018/0214190 A1* | 8/2018 | Erramilli | A61B 17/7082 | |
| 2018/0353225 A1* | 12/2018 | Asaad | A61B 17/7091 | |

* cited by examiner

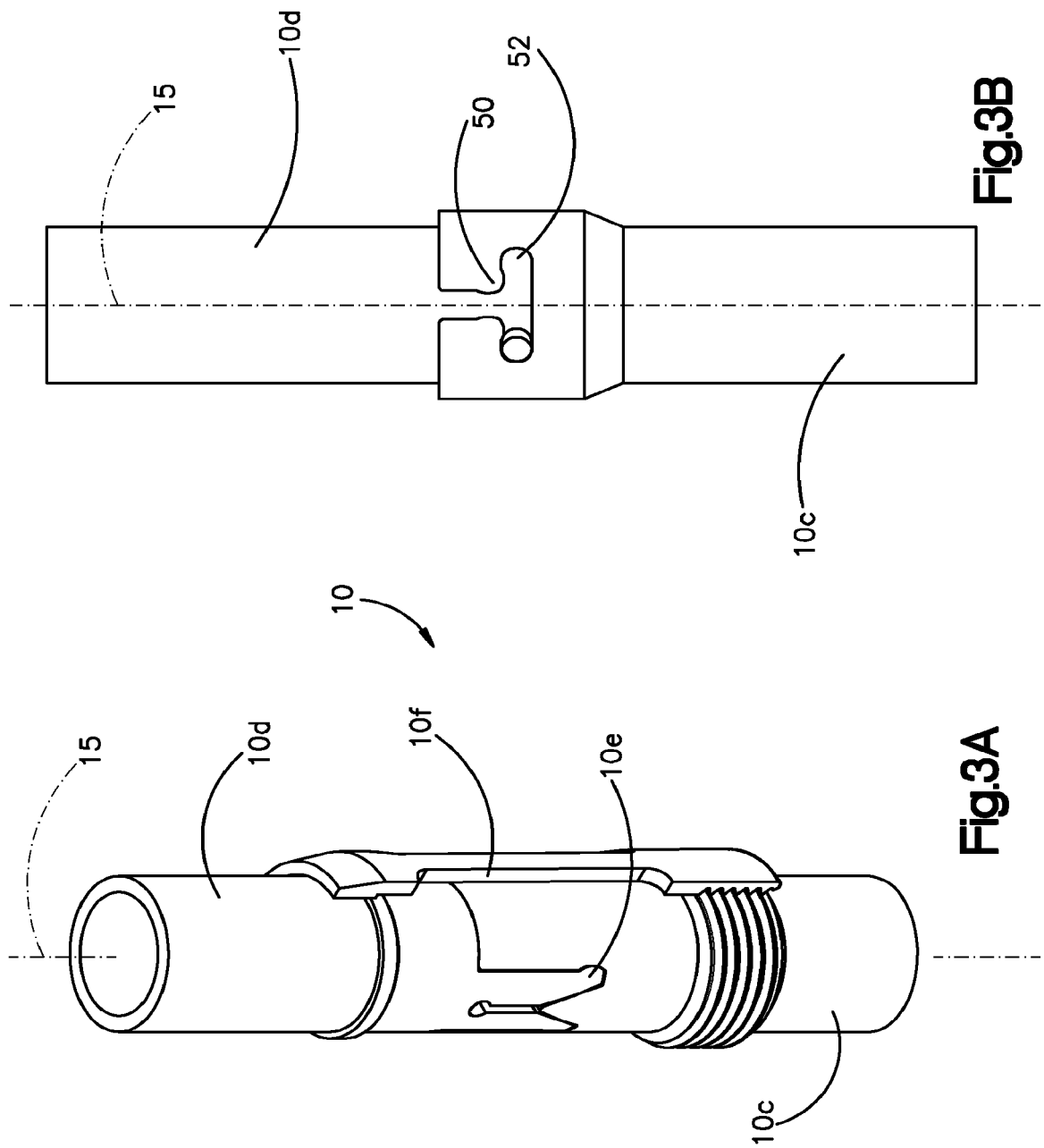

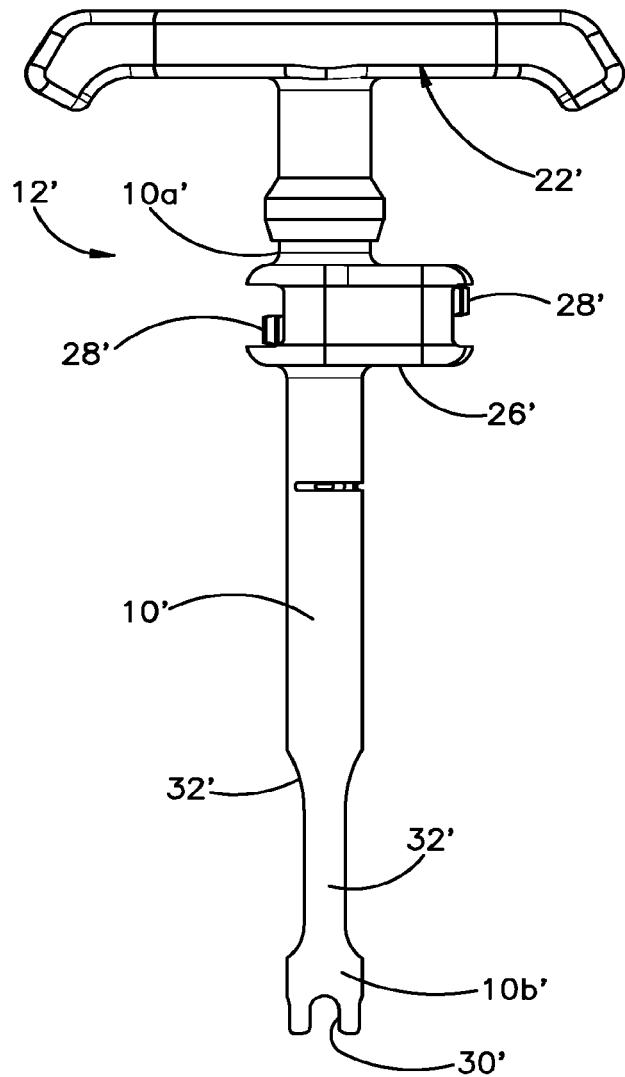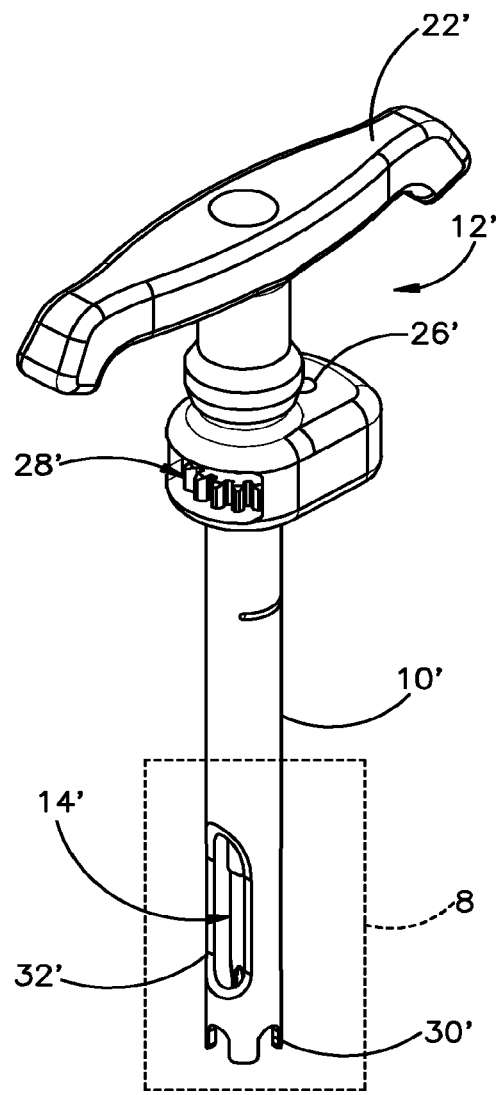
Fig.4
Fig.5

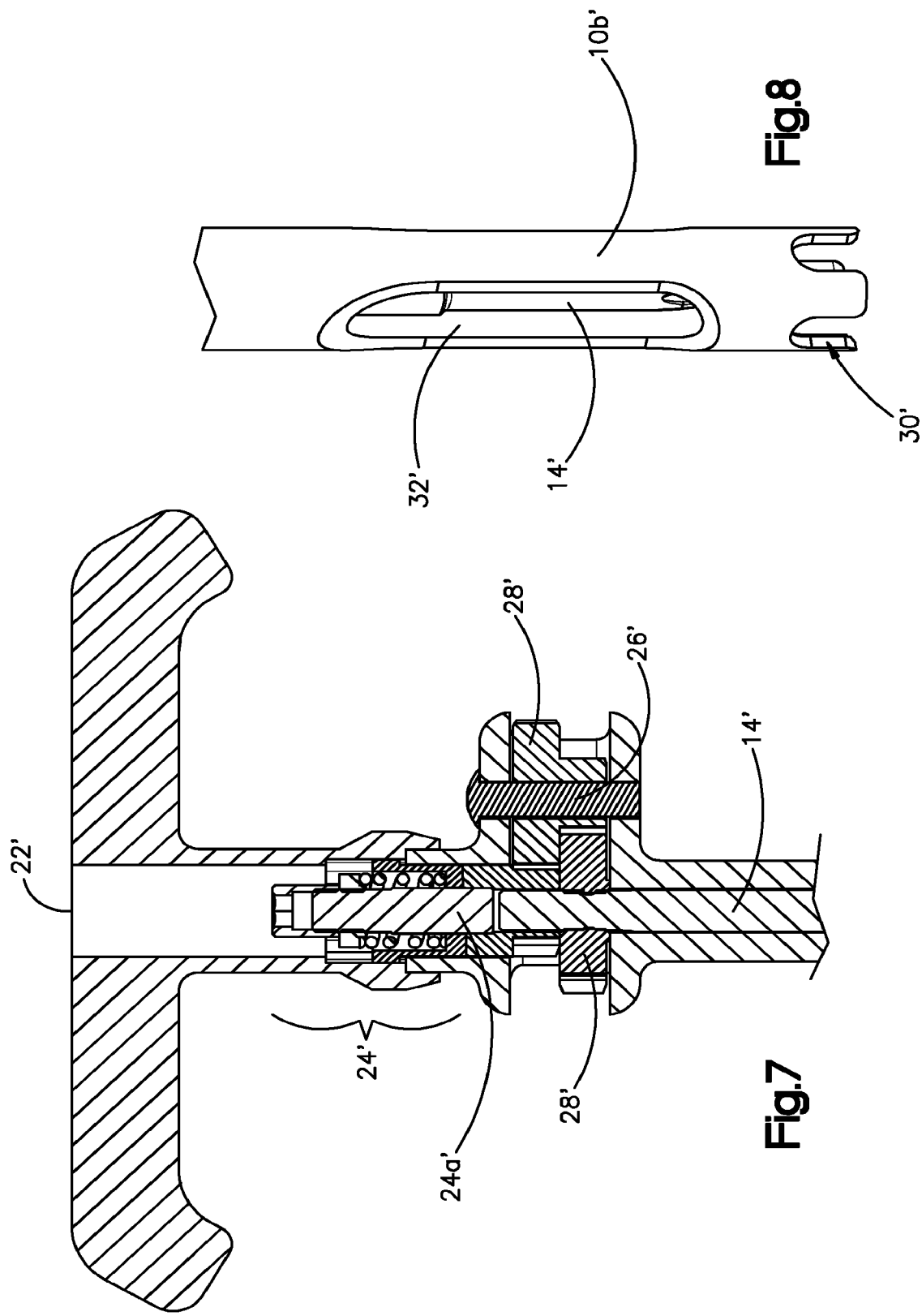

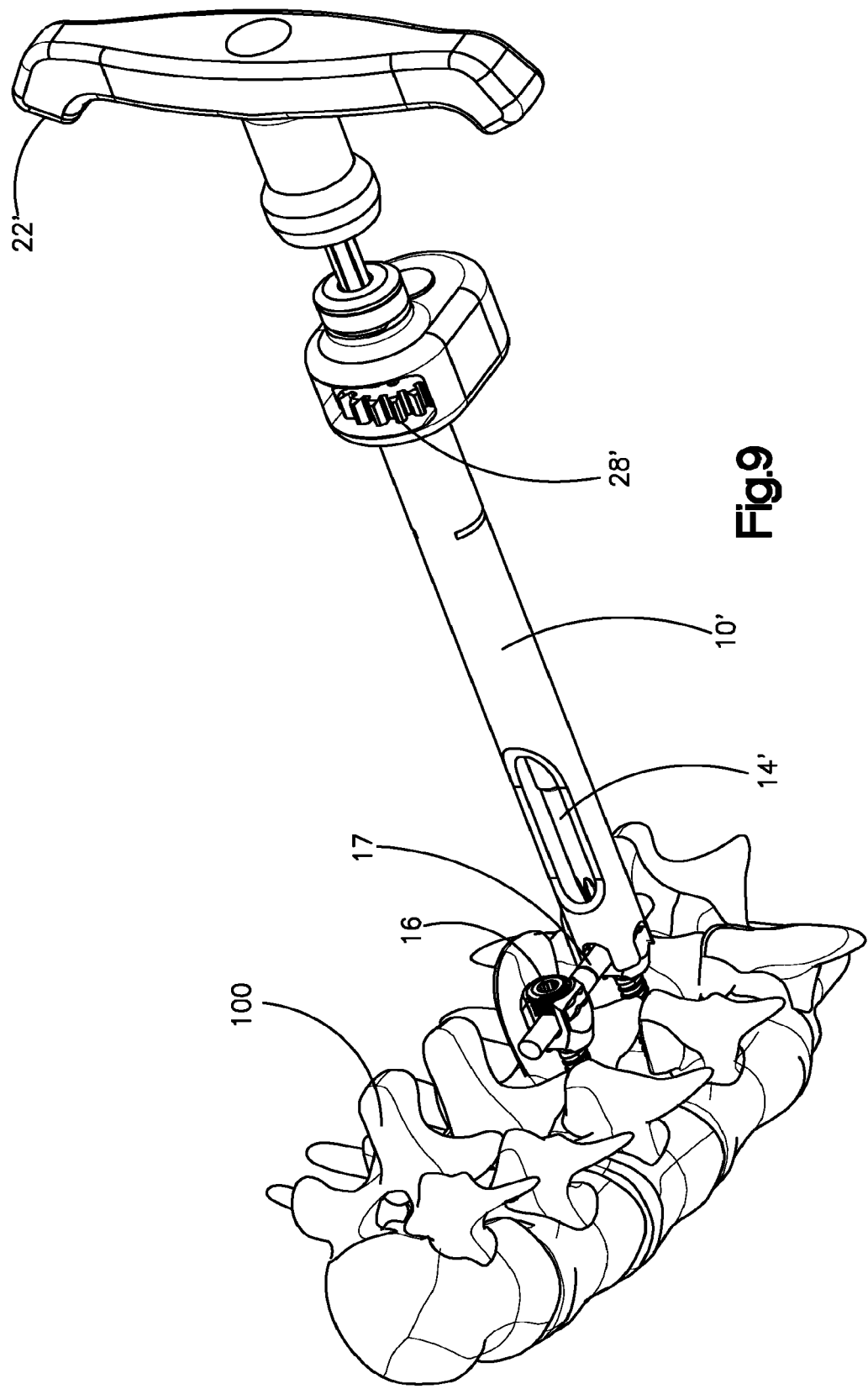

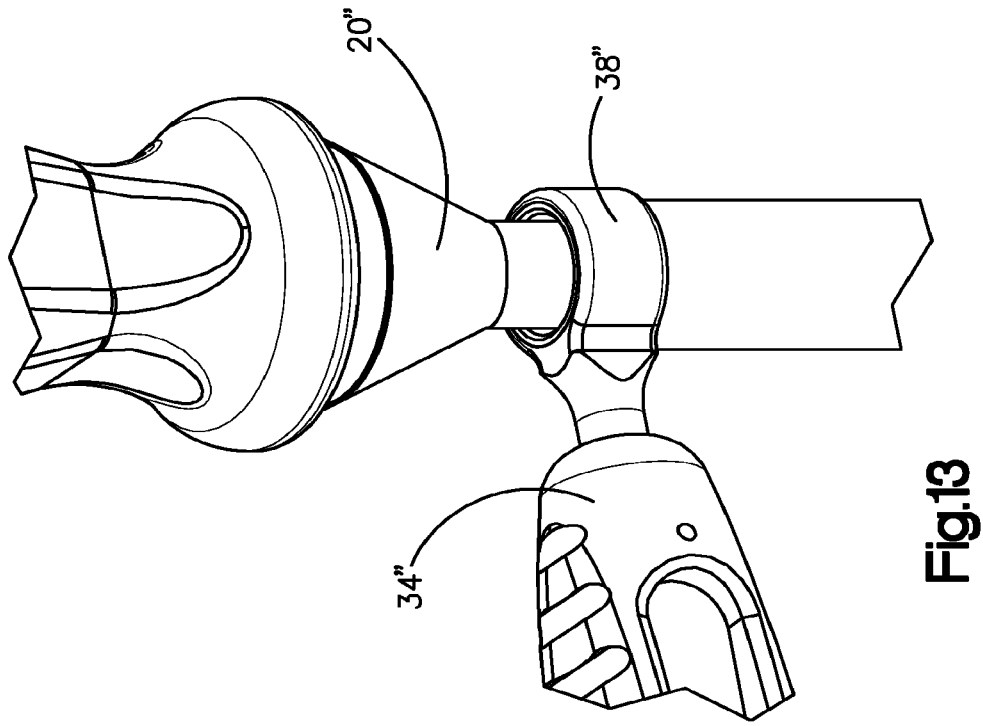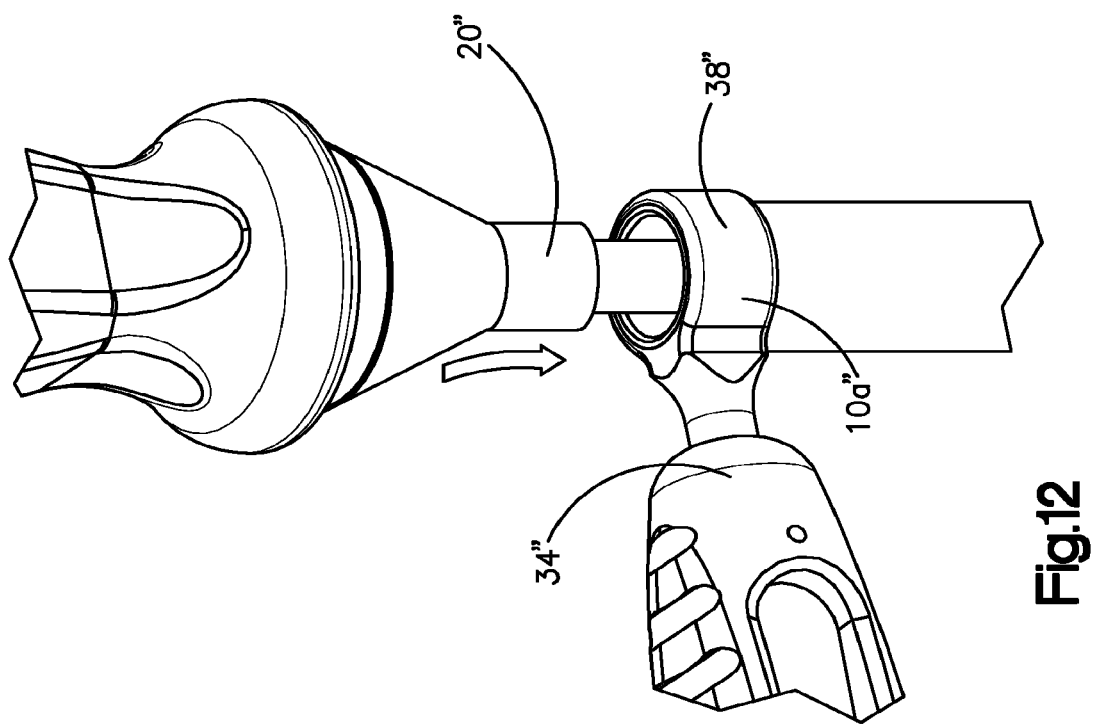

US 11,660,129 B2

TIGHTENING DEVICE FOR SPINE SURGERY

CROSS-REFERENCE TO RELATED APPLICATION

The present invention is a divisional of U.S. patent application Ser. No. 12/901,473, filed Oct. 8, 2010, and claims the benefit of priority to U.S. Provisional Application No. 61/278,671, filed Oct. 9, 2009, and entitled "Anti-Torque Device for Spine Surgery," all of which are incorporated herein by reference in their entirety.

BACKGROUND

The present invention relates to an apparatus and method for performing spine surgery and, more particularly, to a tightening device that may be used for, e.g., spinal surgery that includes an anti-torque or zero-torque device for securing a locking cap or nut to a body of a pedicle screw during spine surgery and a method of using same.

Referring to prior art FIGS. 1A and 1B, the spine 120, also known as the vertebral column or the spinal column, is a flexible column of vertebrae 100 (special types of bones) held together by muscles, ligaments and tendons. The spine 120 extends from the cranium (not shown) to the coccyx 126, encasing a spinal cord 128 and forming the supporting axis of the body (not shown). The spinal cord 128 is a thick bundle of nerve tissue (nerves) that branches off to various areas of the body for the purposes of motor control, sensation, and the like. The spine 120 includes seven cervical vertebrae (not shown), twelve thoracic vertebrae (not shown), five lumbar vertebrae, $L^I$-$L^V$, five sacral vertebrae, $S^I$-$S^V$, and three coccyx vertebrae 126. The sacral and coccyx vertebrae are each fused, thereby functioning as a single unit. FIG. 1B shows the lumbar region 122, the sacral region 124 and the coccyx 126 of the spine 120 and that the vertebrae 100 are stacked one upon another. The top portion 100a and bottom portion 100b of each vertebrae 100 is slightly concave. The opposing concave vertebral surfaces form the intervertebral space 121 in which an intervertebral disk (not shown) resides. Each of the intervertebral disks has a soft core referred to as a nucleus pulposus or nucleus (not shown).

In FIG. 1A, directional arrow 101a is pointing in the posterior direction and directional arrow 101b is pointing in the anterior direction. FIG. 1A shows that each vertebrae 100 includes a body 106 in the innermost portion, a spinal canal 108 and a spinous process 102 at the posterior-most end of the vertebra 100. The vertebrae 100 are substantially similar in composition, but vary in size from the larger lumbar to the smallest coccyx vertebrae 126. Each vertebrae 100 further includes two transverse processes 104 located on either side and a protective plate-like structure referred to as a lamina 110. Nerves from the spinal cord 128 pass through the spinal canal 108 and foramina 111 (FIG. 1B) to reach their respective destinations within the body.

The natural aging process can cause a deterioration of the intervertebral disks and, therefore, their intrinsic support, strength and stability is diminished. Sudden movements may cause a disk to rupture or herniate. A herniation of the disk is primarily a problem when the nucleus pulposus protrudes or ruptures into the spinal canal 108 placing pressure on nerves, which in turn causes spasms, tingling, numbness, and/or pain in one or more parts of the body, depending on the nerves involved. Further deterioration of the disk can cause the damaged disk to lose height and as bone spurs develop on the vertebrae 100, result in a narrowing of the spinal canal 108 and foramen 111, and thereby causes pressure on the nerves emanating from the spinal cord 128.

Presently, there are several techniques, in addition to non-surgical treatments, for relieving the symptoms related to intervertebral disk deterioration. Surgical options include chemonucleolysis, laminectomy, diskectomy, microdiskectomy, and spinal fusion. After spine surgery, adjacent vertebrae 100 may require a fixation system to be clamped to the side where the surgeon accessed the gap between the vertebrae 100. As seen in FIG. 2A, the typical fixation system includes installing pedicle screws 146 in each vertebra 100 and placing a preferably rigid fixation rod 147 within a generally U-shaped body 146b of the screws 146. The rod 147 is typically locked or held in place by a locking cap or nut 148 (FIG. 2A) that may be threaded onto or into a proximal end or U-shaped body 146b of each pedicle screw 146. Examples of prior art pedicle screws, fixation rods and locking caps are described in U.S. Pat. Nos. 5,520,689 and 7,585,315 and U.S. Patent Application Publication No. 2008/0294202 (copies of each attached), which are herein incorporated by reference in their entirety.

As seen in prior art FIGS. 2 and 2A, to ensure a secure connection between the pedicle screw 146, fixation rod 147 and locking cap 148, a surgeon typically uses a manual, hand-actuated screwdriver, generally designated 130, to tighten the locking cap 148 at a predetermined locking torque $T_L$ on a head or U-shaped body 146b of the pedicle screw 146. As is known in the art, an anti-torque device, generally designated 140, having a handle 142 and a shaft 144, may be attached to a portion of the screwdriver 130, such as a shaft 132 of the screwdriver 130, and attached to one of the pedicle screw 146, the locking cap 148 and the fixation rod 147, to allow the surgeon to provide a generally equal and opposite reaction torque $T_R$ to the locking torque $T_L$ applied by the screwdriver 130. In operation, the locking torque $T_L$ is generated by rotational movement (i.e., clockwise) by one of the surgeon's hands, which travels through the shaft 132 of the screwdriver 130, then through the locking cap 148 and finally to the head or U-shaped body 146b of the pedicle screw 146. The generally equal and opposite reaction torque $T_R$ is generated by rotational movement (i.e., counterclockwise, typically by holding the handle 142 in a static location) by the other hand of the surgeon, which travels through the anti-torque device 140 and to the head or U-shaped body 146b of the pedicle screw 146.

The above-identified method of tightening the locking cap 148, rod 147 and pedicle screw 146 requires a relatively large locking torque $T_L$, requires the surgeon or other user to employ both hands and may require significant physical effort by the surgeon. As a result, this method often causes fatigue to the surgeon, especially considering that this method may be performed toward the end of a long day of surgery or at the end of a long surgery that attaches a plurality of screws. Furthermore, it can be difficult to produce a perfectly balanced reaction torque $T_R$, which helps to eliminate additional injury to the patient. In addition, applying the reaction torque $T_R$ may lead to an excessive force load on the screwdriver 130, the anti-torque device 140 and/or connecting soft tissue of the patient, which may result in additional injury to the patient.

Therefore, it would be desirable to provide an anti-torque device for spine surgery that overcomes the above-identified deficiencies. Specifically, it would be desirable to provide an anti-torque device that rotatably fixedly and axially removably attaches to at least a portion of a torque-generating body, such as a hand-actuated screwdriver or electric power driver, that allows a surgeon or other user to apply a locking torque and generate a generally equal and opposite reaction torque to the pedicle screw, locking cap and/or fixation rod with only a single hand.

SUMMARY

A device for spinal surgery that may be used for, e.g., tightening a locking cap onto at least a portion of a pedicle screw. In some implementations, the device may include a torque-generating body having a proximal end and an opposing distal end and a drive shaft rotatably driven by the torque-generating body. A proximal end of the drive shaft may be operatively engaged to the distal end of the torque-generating body and an opposing distal end of the drive shaft may engage at least a portion of one of the locking cap and the pedicle screw. An anti-torque device is provided that has an elongated and generally hollow member defining a longitudinal axis. The member has a proximal end and an opposing distal end, where the proximal end of the anti-torque device may be fixed from rotating relative to at least a portion of the torque-generating body.

In other implementations, there is provided an anti-torque device for spinal surgery that includes an elongated and generally hollow member defining a longitudinal axis, the member having a proximal end and an opposing distal end. The proximal end is fixed from rotating relative to a portion of a torque-generating body and the distal end is fixed from rotating relative to at least a portion of one of a pedicle screw, a locking cap, a fixation rod and a clamp.

In yet other implementations, there is provided a method of tightening a locking cap onto a pedicle screw during spine surgery. The method may include providing a torque-generating body having a drive shaft rotatably attached thereto; engaging at least a portion of a drive shaft with a locking cap; rotatably fixedly attaching a first end of an anti-torque device to at least a portion of the torque-generating body; rotatably fixedly attaching a second end of the anti-torque device to at least a portion of one of a pedicle screw, the locking cap, a fixation rod and a clamp; and rotating the drive shaft to apply a locking torque to one of the locking cap and pedicle screw to generate an equal and opposite reaction torque to one of the pedicle screw, the locking cap, the fixation rod and the clamp.

In some implementations, there is provided a surgical device that includes a torque-generating body having a proximal end and an opposing distal end and a gearbox that receives an input torque from the torque-generating body and provides an increased output torque to a drive shaft to rotatably drive the drive shaft. A proximal end of the drive shaft may be operatively engaged to the gearbox and an opposing distal end of the drive shaft engaging at least a portion of one of a locking cap and a pedicle screw. An anti-torque device may be provided that is comprised of an elongated and generally hollow member defining a longitudinal axis. The member has a proximal end and an opposing distal end, where the proximal end of the anti-torque device may be slidably engaged to the gearbox and fixed from rotating relative to at least a portion of the torque-generating body.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE SEVERAL VIEWS OF THE DRAWINGS

The foregoing summary, as well as the following detailed description of embodiments of the invention, will be better understood when read in conjunction with the appended drawings. For the purpose of illustrating the invention, several implementations are shown in the drawings. It should be understood, however, that the invention is not limited to the precise arrangements and instrumentalities shown. In the drawings:

FIG. 3A is an enlarged fragmentary partially cross-sectional view of an alterative embodiment of the anti-torque device from that shown in FIG. 3;

FIG. 3B is an enlarged fragmentary elevation view of another alternative embodiment of the anti-torque device from that shown in FIG. 3;

FIG. 4 is an elevation view of an anti-torque device in accordance with a second embodiment of the present invention, along with a hand-actuated screwdriver;

FIG. 5 is a perspective view of the anti-torque device and hand-actuated screwdriver shown in FIG. 4;

FIG. 7 is a cross-sectional perspective view of the proximal portion of the anti-torque device and hand-actuated screwdriver shown in FIG. 4;

FIG. 8 is an enlarged fragmentary perspective view of a distal portion of the anti-torque device and hand-actuated screwdriver shown in FIG. 4;

FIG. 9 is a perspective view of the anti-torque device shown in FIG. 4 operatively connected to a pedicle screw;

FIG. 12 is an enlarged fragmentary perspective view of a portion of the anti-torque device and power tool shown in FIG. 11, with the power tool shown in an intermediate position with respect to the anti-torque device;

FIG. 13 is an enlarged fragmentary perspective view of a portion of the anti-torque device and power tool shown in FIG. 11, with the power tool shown in a fully engaged position with the anti-torque device;

DETAILED DESCRIPTION OF THE INVENTION

Figure 1B:
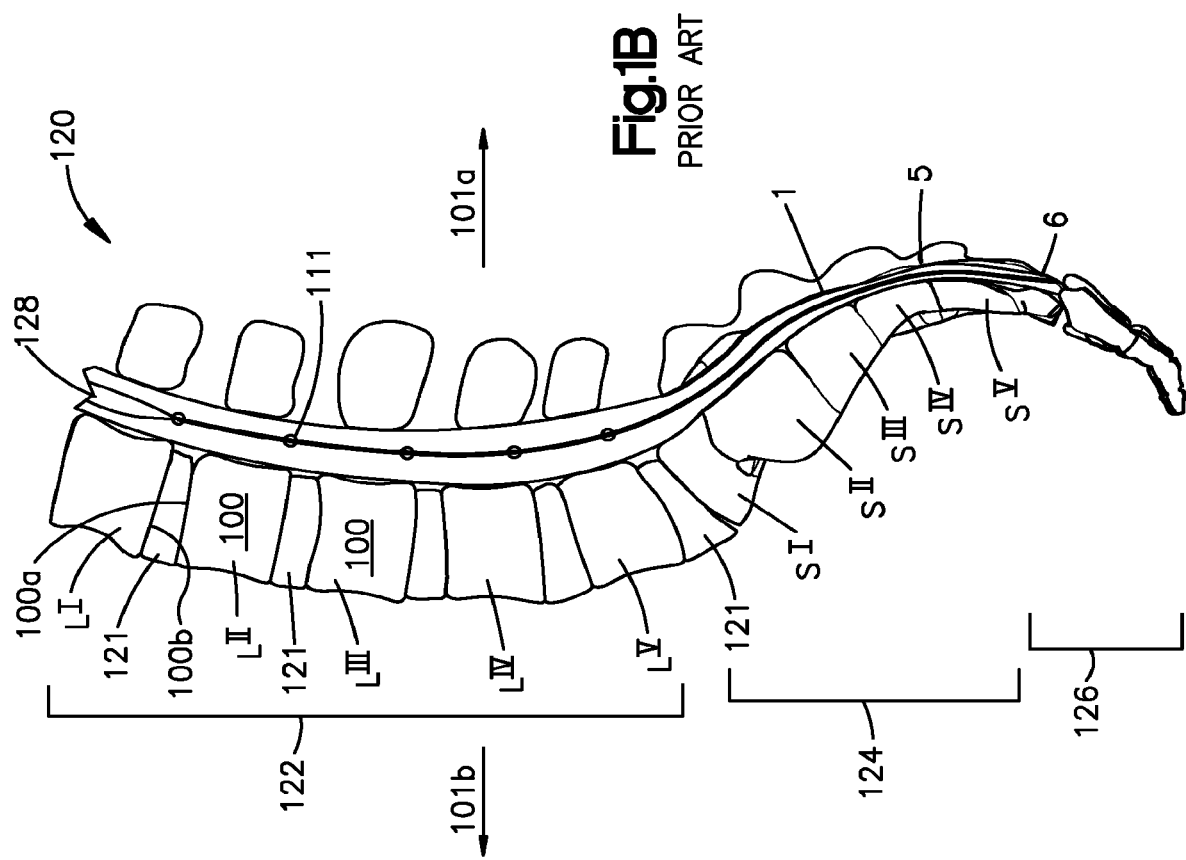
FIG. 1B is a side sectional elevation view of the lumbar and sacral regions of a human spine as is known in the art.
Figure 1A:
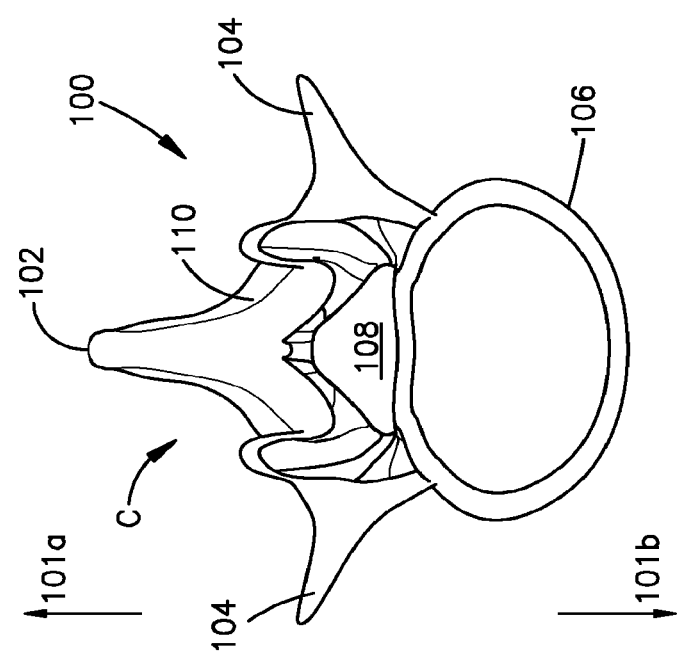
FIG. 1A is a top view of a human vertebrae as is known in the art.

Certain terminology is used in the following description for convenience only and is not limiting. The words "right," "left," "upper," and "lower" designate directions in the drawings to which reference is made. The words "anterior," "posterior," "superior," "inferior" and related words and/or phrases designate preferred positions and locations in the human body to which reference is made and are not meant to be limiting. The words "first" and "second" designate an order of operations in the drawings to which reference is made, but do not limit these steps to the exact order described. The words "inwardly" and "outwardly" refer to directions toward and away from, respectively, the geometric center of the object(s) described herein and designated parts thereof. Additionally, the terms "a," "an" and "the," as used in the specification, mean "at least one." The terminology includes the words above specifically mentioned, derivatives thereof, and words of similar import.

Figure 3:
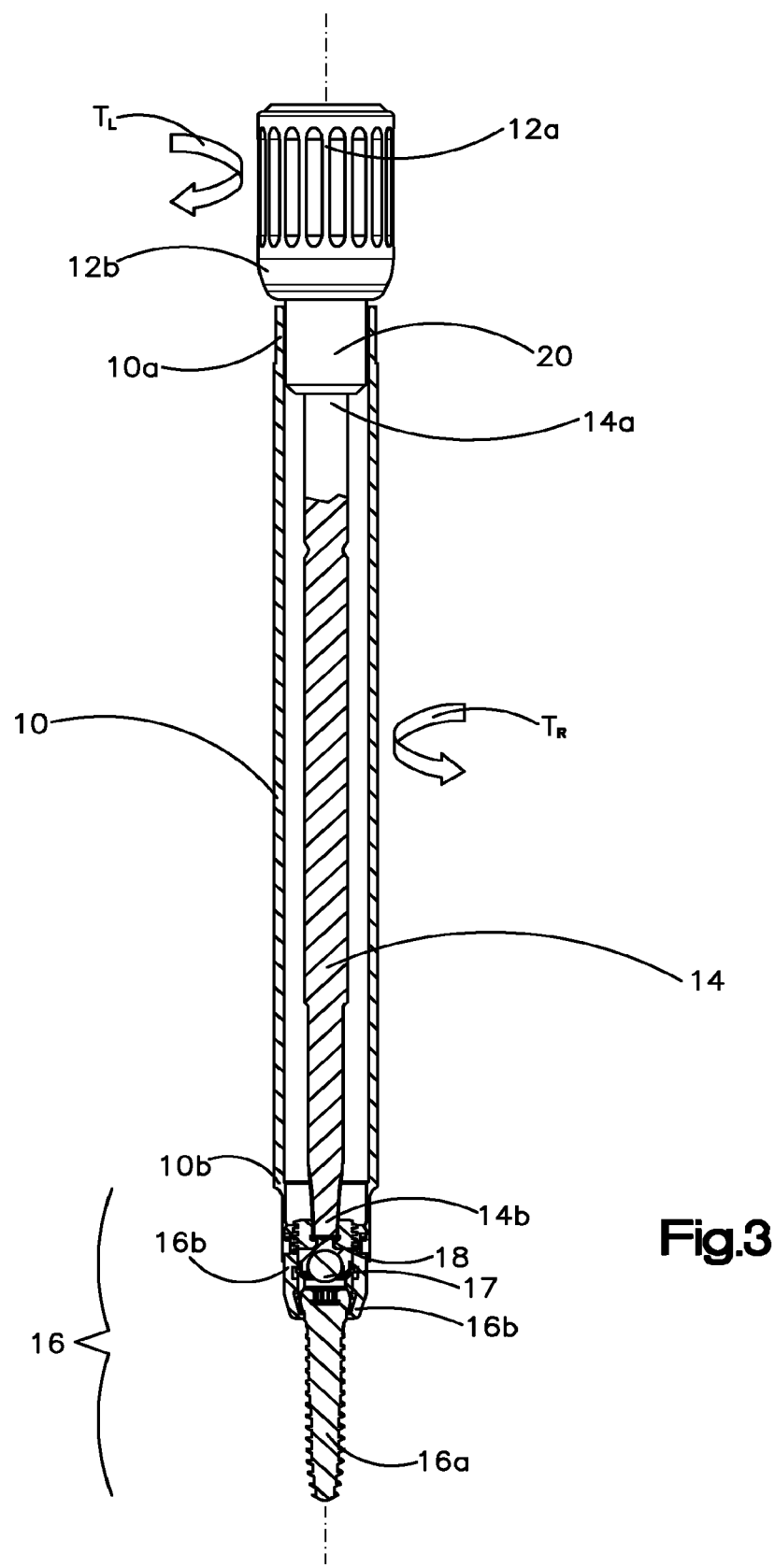
FIG. 3 is a perspective view of an anti-torque device in accordance with a first embodiment of the present invention, along with a power tool and pedicle screw.
Figure 6:
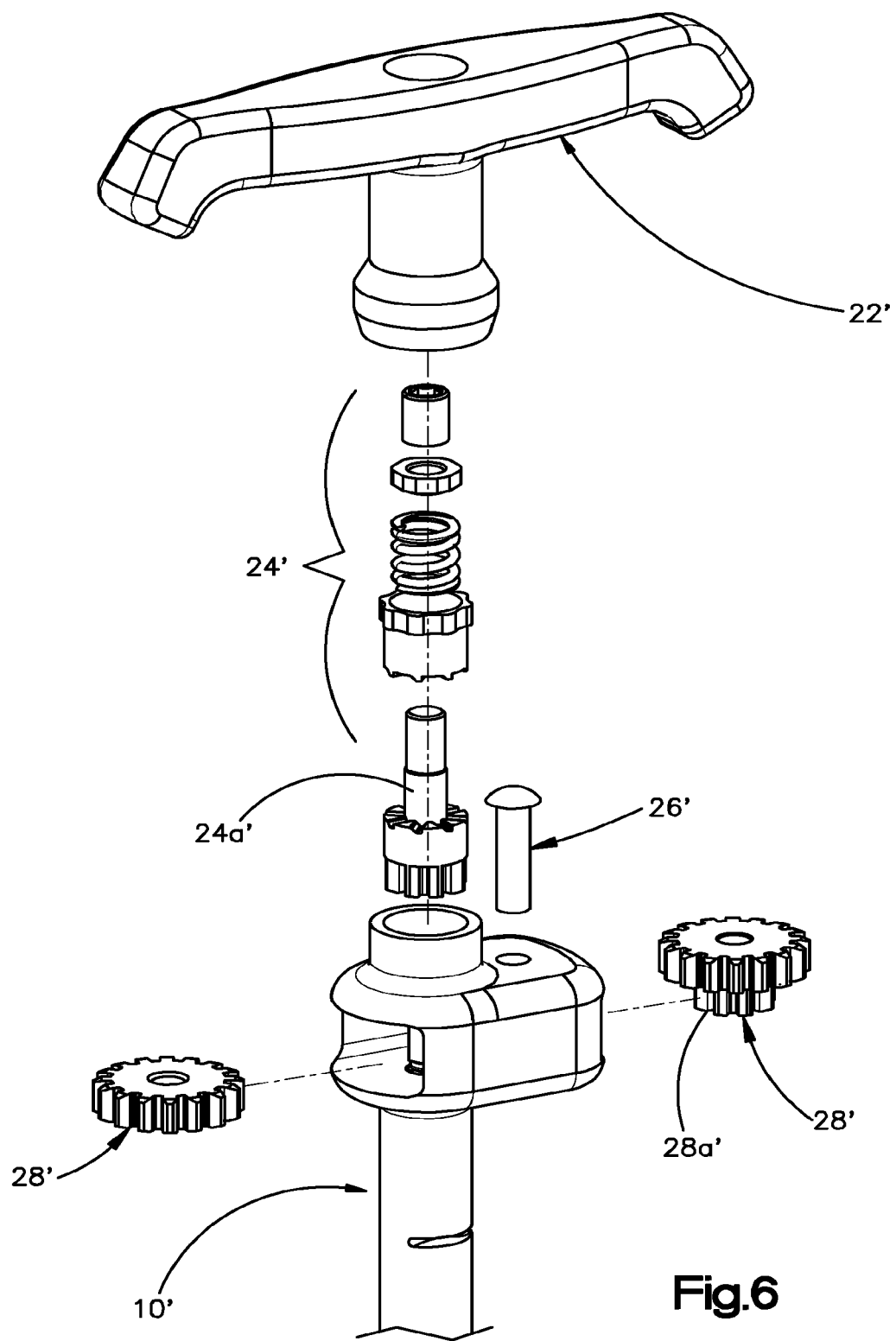
FIG. 6 is an exploded perspective view of a proximal portion of the anti-torque device and hand-actuated screwdriver shown in FIG. 4.

Referring to the drawings in detail, wherein like numerals indicate like elements throughout, there is shown in FIG. 3 a first embodiment of a combined anti-torque or counter-torque device, generally designated 10, a torque-generating body, generally designated 12, having a drive shaft 14 operatively connected thereto, a pedicle screw 16, a locking cap or nut 18 and a preferably generally rigid fixation rod 17. The anti-torque device 10 and torque-generating body 12 allow a user, such as a surgeon, to create a generally balanced reaction between a locking torque $T_L$ generated by the drive shaft 14 of the torque-generating body 12 on one of the treaded cap 18 and pedicle screw 16 and a generally equal and opposite reaction torque $T_R$ generated by the anti-torque device 10 on one of the treaded cap 18, pedicle screw 16 and fixation rod 17.

The fixation rod 17 is an internally-mounted device, with respect to a patient, for fixing two or more adjacent vertebrae after a surgical procedure such as installing a fusion cage (not shown) and the like. The pedicle screw 16 preferably includes a bone screw, thread or anchor 16a at a distal portion and a machine or other mating thread (not shown) at a proximal portion or body 16b. The proximal portion of the pedicle screw 16 may define a U-shaped groove and the machine thread is preferably adapted to receive at least a portion of the treaded cap 18. The pedicle screw 16 may be polyaxial or monoaxial. For the sake of brevity, specific discussion of mounting the pedicle screw(s) 16, cap(s) 18 and fixation rod 17 is omitted herein. Those of ordinary skill in the art recognize how the pedicle screw(s) 16 is/are attached to a vertebrae 100, how the fixation rod 17 is attached to the pedicle screw(s) 16, and how the locking cap 18 is attached to each pedicle screw 16. The pedicle screw(s) 16, fixation rod 17 and locking cap 18 generally comprise an internal fixation system for securing together adjacent vertebrae 100.

Referring again to FIG. 3, in the present embodiment, the torque-generating body 12 is a power tool, such as an electric driver, having a motor (not shown) and a power supply (not shown), such as a battery or a conventional power cord to operatively engage an electrical outlet. The torque-generating body 12 may alternatively be powered by pressurized fluid, such as air or a pressurized liquid. However, the torque-generating body 12 may be a conventional, hand-actuated/operated screwdriver or virtually any other device capable of performing the functions of the torque-generating body 12 described herein. Preferably, the torque-generating body 12 has a proximal end 12a for receiving at least a portion of one of the user's hand and an opposing distal end 12b. The distal end 12b of the torque-generating body 12 may include a motor shaft 20 that extends therefrom.

The drive shaft 14 is preferably rotatably attached to at least a portion of the torque-generating body 12 and is rotatably driven by the torque-generating body 12. However, in the embodiment employing a hand-actuated screwdriver, the drive shaft 14 may be fixedly attached to the handle of the screwdriver. In the present embodiment, a proximal end 14a of the drive shaft 14 is operatively, and preferably rotatably, engaged to the distal end 12b of the torque-generating body 12 and an opposing distal end 14b of the drive shaft 14 engages at least a portion of one of the locking cap 18 and pedicle screw 16. The drive shaft 14 preferably defines a longitudinal axis 13 between the proximal and distal ends 14a, 14b.

Preferably, the anti-torque device 10 is an elongated and generally hollow member that defines a longitudinal axis 15 generally extending from a first or proximal end 10a of the anti-torque device 10 to an opposing second or distal end 10b of the anti-torque device 10. The proximal end 10a of the anti-torque device 10 is preferably rotatably fixedly attached to and/or fixed from rotating relative to at least a portion of the torque-generating body 12 so as to not rotate with the drive shaft 14. However, the proximal end 10a is preferably not axially and/or pivotally fixed to the torque-generating body 12, such that the anti-torque device 10 is removably attached to the torque-generating body 12.

The distal end 10b of the anti-torque device 10 is preferably rotatably fixedly attached to and/or fixed from rotating relative to at least a portion of one of the pedicle screw 16, locking cap 18 and the fixation rod 17. However, the distal end 10b is preferably not axially and/or pivotally fixed to one of the pedicle screw 16, locking cap 18 and the fixation rod 17, such that the anti-torque device 10 is removably attached to the pedicle screw 16, locking cap 18 and the fixation rod 17.

As seen in FIGS. 3A and 3B, at least a portion of the anti-torque device 10 may be selectively interchangeable to fit various types, sizes and/or shapes of pedicle screws 16, locking caps 18 and/or fixation rods 17. Thus, a generally more proximal portion of the anti-torque device 10 may selectively engage at least a portion of one or more generally unique distal portions of the anti-torque device 10. Specifically, as seen in FIG. 3A, a lower portion or tube 10c of the anti-torque device 10 may frictionally engage an upper portion or tube 10d, such as by a mating wedge engagement 10e. Further, a connecting tube 10f may be slidingly received over at least a portion of the lower and upper tubes 10c, 10d and threadingly engagable with at least a portion of one of the tubes 10c, 10c. Alternatively, as seen in FIG. 3B, the lower tube 10c may be rotatingly engagable with the upper tube 10d. In the embodiment of FIG. 3B, either the lower or upper tube 10c, 10d preferably includes a bump or projection 50 that surrounds and/or extends into at least a portion of a slot or groove 52. The projection 50 generally prevents accidental removal of the upper tube 10d from the lower tube 10c by requiring the surgeon or other user to turn (i.e., rotate horizontally) and pull (i.e., slide axially) to separate the tubes 10c, 10d. Alternatively, the lower and upper tubes 10c, 10d may include a mating spline connection or a bayonet attachment (not shown). Each of the above-identified features allows the surgeon or other user to modify the anti-torque device 10 depending upon the various hardware (i.e., screws, caps, rods) during surgery, thus resulting in a generally modular anti-torque device 10.

An interior surface of the distal end 10b of the anti-torque device 10 may include one or more generally equally spaced-apart recesses, notches, lugs and/or ridges (not shown) that extend generally perpendicularly therefrom to engage at least a portion of one of the pedicle screw 16, locking cap 18 and the fixation rod 17. Alternatively or additionally, the distal end 10b of the anti-torque device 10 may have a generally ovular or not-perfectly-circular cross-sectional shape to engage at least a portion of one of the pedicle screw 16, locking cap 18 and the fixation rod 17. In the present embodiment, the anti-torque device 10 generally surrounds at least a portion of the drive shaft 14, such that the longitudinal axis 13, 15 of each are parallel and/or coincide.

The anti-torque device 10 may be designed to selectively accommodate either a power driver, as shown in FIG. 3, or a hand-actuated screwdriver (now shown in FIG. 3). Specifically, a portion of the anti-torque device 10 and/or drive shaft 14 may be formed of two (2) or more selectively separable portions or segments. For example, the portions of the anti-torque device 10 and/or drive shaft 14 may include a mating tongue-and-groove or bayonet arrangement. For example, in operation, a surgeon or other user may initially operatively engage a power driver to the anti-torque 10 and/or drive shaft 14. Then, at a later point, the surgeon may selectively disengage the two (2) portions of the anti-torque device 10 and/or drive shaft 14 to operatively engage a hand-actuated driver to the anti-torque device 10 and/or drive shaft. Thus, the anti-torque device 10 and/or drive shaft 14 may operatively engage with more than one generally unique torque-generating body 12 or other driving unit. Those of ordinary skill in the art would appreciate that different driving units can be advantageous for generating different types and/or amounts of torque and rotational speed.

The torque-generating body 12 may include a clutch (not shown) to release the torque to disengage the torque-generating body 12 from the pedicle screw 16 and/or locking cap 18. The clutch may be selectively manually operated by the surgeon through a push button (not shown) or may be automatically activated to set the torque applied by the torque-generating body 12 at or close to zero.

Most, if not all, components of the anti-torque device 10 and the torque-generating body 12 are formed of a high-strength material, such as a metallic material. For example, in the embodiment, the anti-torque device 10 and at least the drive shaft 14 of the torque-generating body 12 are formed of a type of stainless steel. However, the anti-torque device 10 and the torque-generating body 12 are not limited to such materials. For example, alternate materials may include titanium and its alloys, aluminum and its alloys, polymers, phenolic and/or silicone.

Tightening the treaded cap 18 onto a pedicle screw 16 may be done as follows:

(i) mounting a first end of the fixation rod 17 to one pedicle screw 16 and mounting a second end of the fixation rod 17 to another pedicle screw 16;

(ii) mounting the locking cap 18 onto each pedicle screw 16 over the fixation rod 17;

(iii) attaching the distal end 14b of the drive shaft 14 of the torque-generating body 10 to at least a portion of one of the locking cap 18 and pedicle screw 16;

(iv) attaching the distal end 10b of the anti-torque device 10 to at least a portion of one of the pedicle screw 16, a portion of the locking cap 18, the fixation rod 17 or virtually any other structure fixedly secured to one of the screw 16, cap 18 and/or rod 17; and (v) rotating the drive shaft 14 (i.e., clockwise) to apply a locking torque $T_L$ to the locking cap 14, while preventing the pedicle screw 16 from rotating, thereby generating an equal and opposite reaction torque $T_R$ (i.e., counterclockwise) to the pedicle screw 16 or fixation rod 17.

The procedure may be performed with working channels or tubes that include a slot at the distal-most portion of the working channels or tubes for facilitating the complex dexterous work to be performed, such as screwing in the pedicle screws 16, fixation rods 17 and/or tightening mounting hardware, such as the locking caps 18 and the like.

Referring to FIGS. 4-10, a second embodiment of a combined anti-torque device and a torque-generating body, generally designated 10' and 12', respectively is shown. Like numerals are utilized to identify like elements and a prime symbol (') is utilized to distinguish like components of the anti-torque device 10' and torque-generating body 12' of the second embodiment from those of the first embodiment. The torque-generating body 12' of the second embodiment is preferably hand-actuated. Specifically, a proximal end of the torque-generating body 12' includes an input or T-shaped handle 22' to allow the user to rotate the drive shaft 14' with a single hand. Enclosed within a portion of the anti-torque device 10' is a torque limiting mechanism 24' (FIGS. 6 and 7), an idler shaft 26' and spur gears 28' (forming a gearbox), which reduce the required torque input and increase the torque output of the drive shaft 14'. However, the torque-generating body 12' may alternatively be a straight inline manual handle or a power driver, each either integrally formed with the gearbox, or selectively detachable therefrom.

In this embodiment, a first gear 24a' is operatively connected to a distal end of the torque limiting mechanism 24' and operatively engages a first spur gear 28'. The first spur gear 28' preferably has twice the number of gear teeth as the first gear 24a', such as a twenty (20) to ten (10) gear tooth ratio. A spur 28a' of the first spur gear 28' operatively engages a second spur gear 28'. The second spur gear 28' preferably has twice the number of gear teeth as the spur 28a' of the first spur gear 28', such as a twenty (20) to ten (10) gear tooth ratio. The proximal end 14a' of the drive shaft 14' is operatively engaged with the second spur gear 28'. In an embodiment, at least a portion of the proximal end 14a' of the drive shaft 14' extends through at least a central portion of the second spur gear 28' and is fixedly connected thereto, such that rotation of the second spur gear 28' directly rotates the drive shaft 14'. Thus, rotation of the first gear 24a' by or through the torque limiting mechanism 24' rotates the drive shaft 14' and increases the torque applied by the surgeon. In some implementations, the overall gear ratio of the gearbox maybe 4-to-1, with a range between 2-to-1 and 10-to-1.

As with the first embodiment, a proximal end 10a' of the anti-torque device 10' is preferably rotatably fixedly attached to at least a portion of the torque-generating body 12'. A distal end 10b' of the anti-torque device 10' preferably rotatably fixedly attaches to one of a pedicle screw 16, and fixation rod 17 that is part of the internal fixation system. In operation, rotation of the T-shaped handle 22' rotates the drive shaft 14' with respect to the anti-torque device 10'. Thus, the drive shaft 14' applies a locking torque on one of the locking cap 18 and the pedicle screw 16, while the anti-torque device 10' prevents the pedicle screw 16 from rotating and, thus, a generally equal and opposite reaction torque is applied to at least one of the pedicle screw 16, locking cap 18, fixation rod 17 and clamp. As with the first embodiment, the above-identified structure of the second embodiment allows the user to accomplish proper tightening of the locking cap 18 to the pedicle screw 16 with only a single hand.

Figure 10:
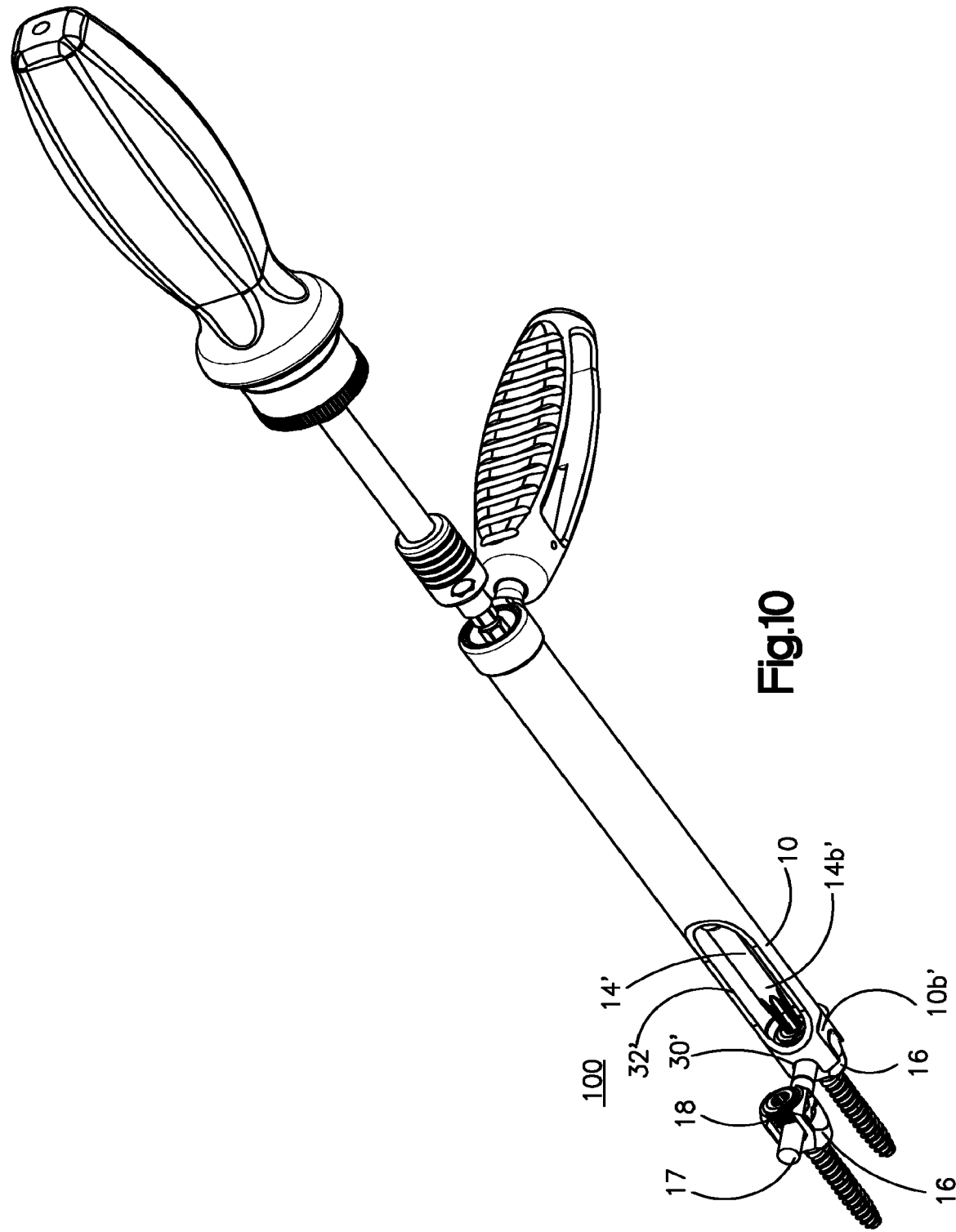
FIG. 10 is a perspective view of the distal portion of anti-torque device and hand-actuated screwdriver shown in FIG. 4 operatively engaged with one of a pedicle screw, a treaded cap and a fixation rod.

As seen in FIGS. 4, 5 and 8-10, the distal end 10b' of the anti-torque device 10' preferably includes at least one but preferably four (4) generally equally, radially spaced-apart archways 30' that extend radially inwardly from the distal end 10b'. The archways 30' provide clearance for at least a portion of the fixation rod 17 (FIGS. 9 and 10) during operation of the anti-torque device 10' and the torque-generating body 12'. In operation, at least a portion of one of the archways 30' preferably contacts or engages at least a portion of the fixation rod 17 (FIGS. 9 and 10) to generally hold the distal end 10b' of the anti-torque device 10' stationary. Further, in some implementations, two (2) equally radially spaced-apart cut-outs or openings 32' may be formed in a side wall of the anti-torque device 10' to allow the user to visualize connection and rotation of the distal end 14b' of the drive shaft 14' and the locking cap 18 (FIG. 10). The anti-torque device 10' may be provided with fewer or additional openings 32'.

Figure 2:
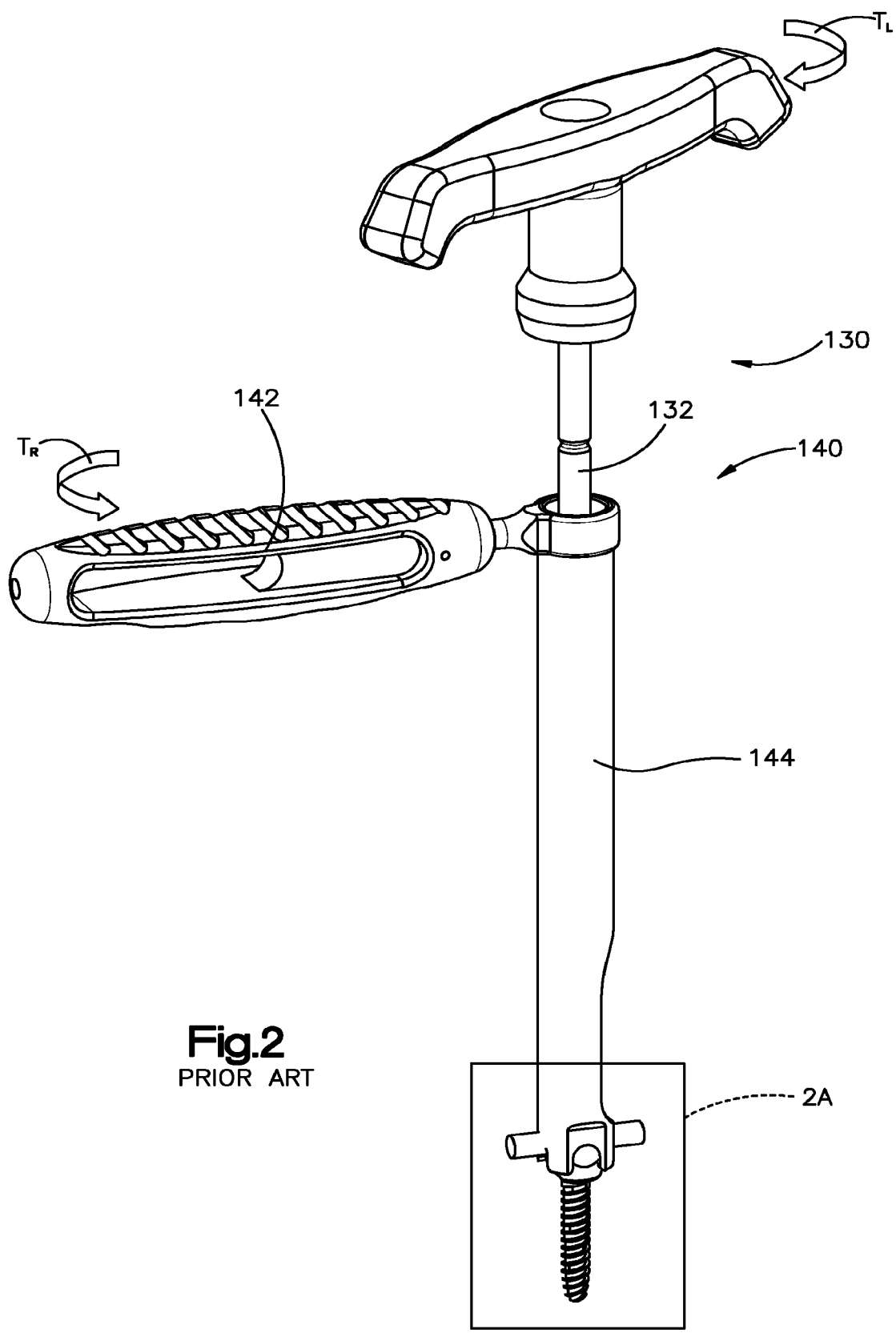
FIG. 2 is a perspective view of a hand-actuated screwdriver and anti-torque device as is known in the art.
Figure 2A:
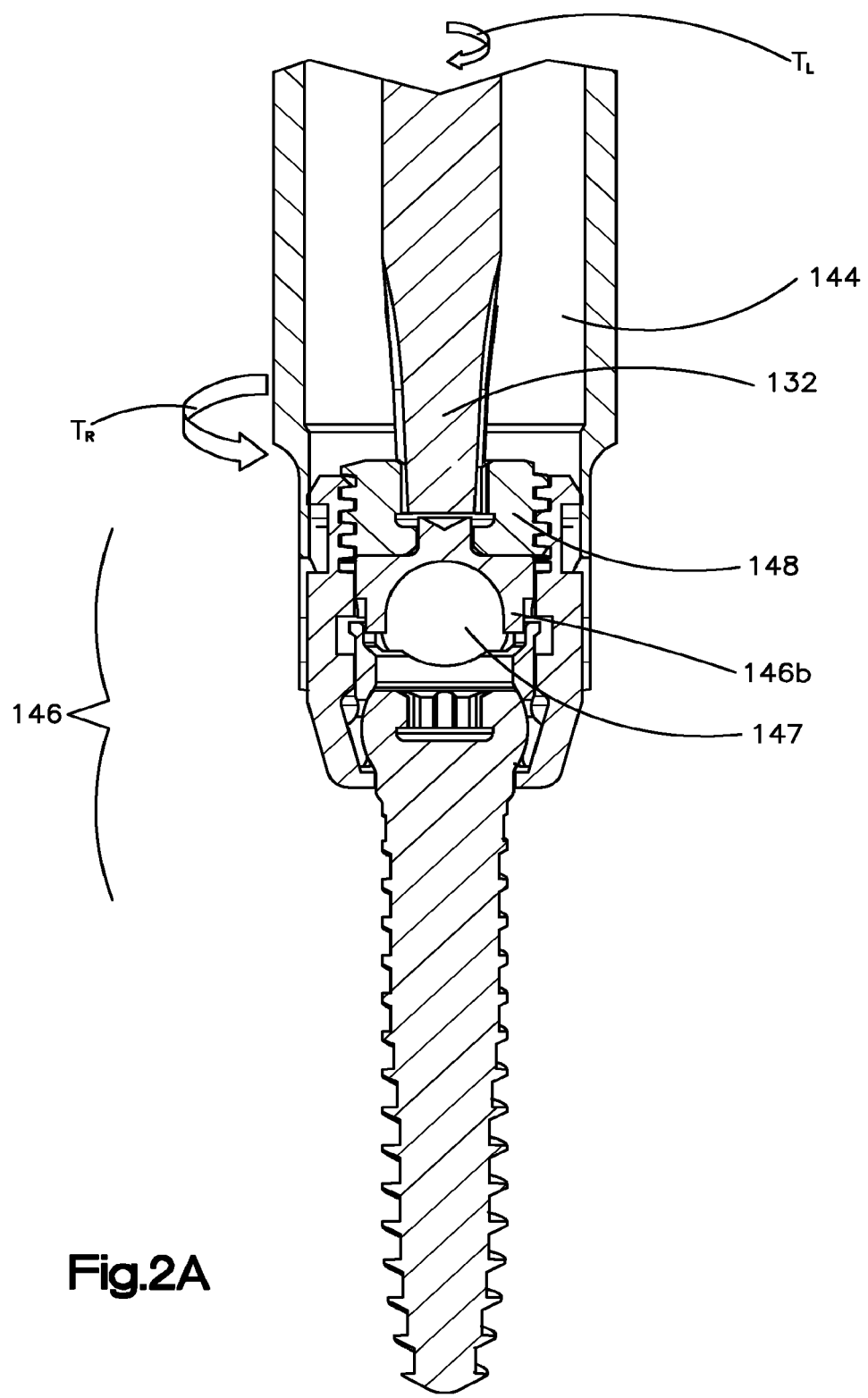
FIG. 2A is an enlarged fragmentary cross-sectional elevation view of a distal end of the screwdriver and anti-torque device and a proximal end of a pedicle screw as shown in FIG. 2.
Figure 11:
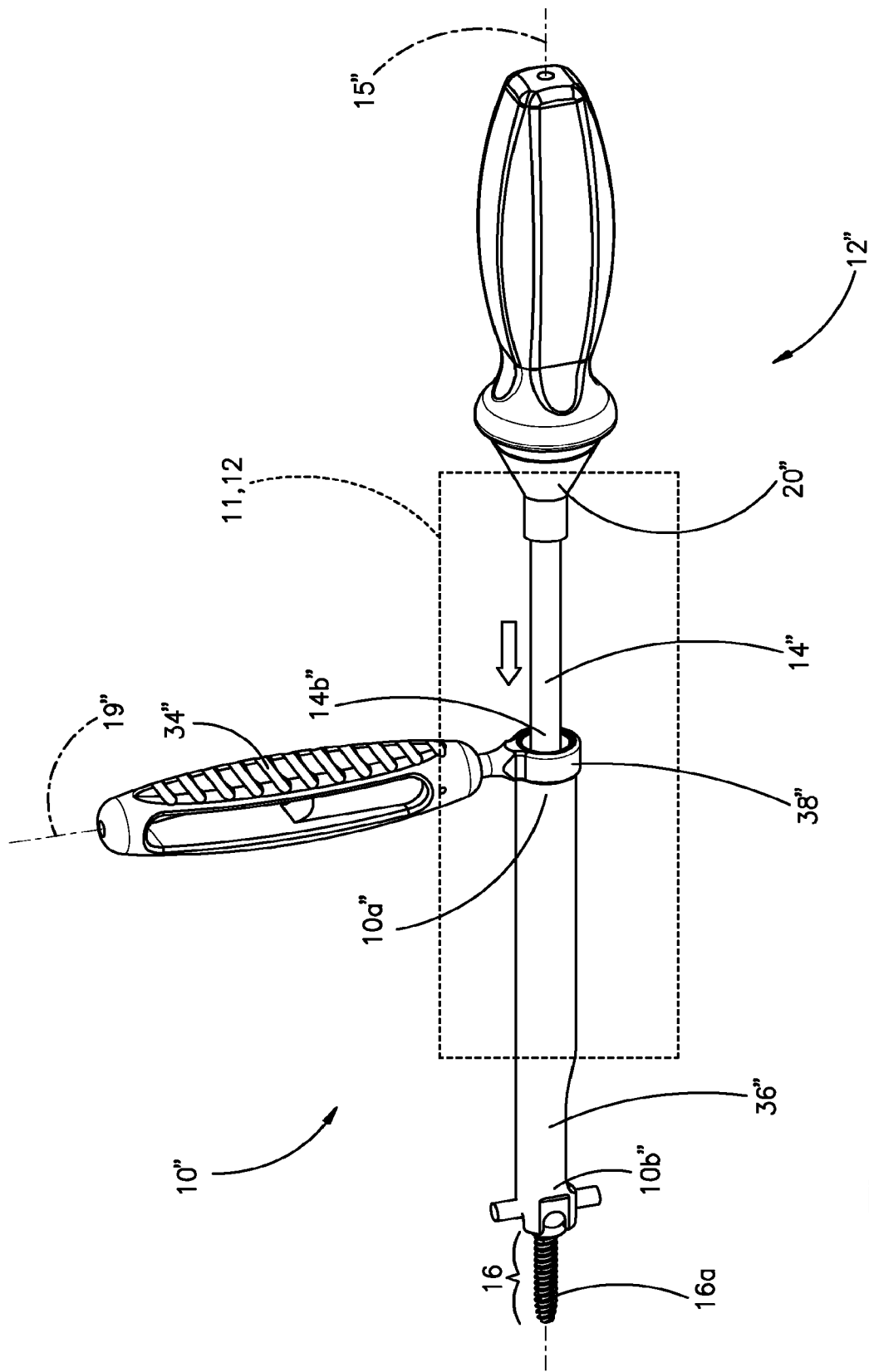
FIG. 11 is a perspective view of an anti-torque device in accordance with a third embodiment of the present application, along with a power tool and pedicle screw, wherein the power tool is shown in an extended position with respect to the anti-torque device.

Referring to FIGS. 11-13, a third embodiment of a combined anti-torque device and a torque-generating body, generally designated 10" and 12", respectively, is shown. Like numerals are utilized to identify like elements and two (2) prime symbols (") are utilized to distinguish like components of the anti-torque device 10" and torque-generating body 12" of the third embodiment from those of the first and second embodiments. The torque-generating body 12" of the third embodiment is a power tool similar to that employed in the first embodiment (FIG. 3). However, a conventional hand-actuated screwdriver may easily replace the power tool by sliding a drive shaft 14" of the torque-generating body 12" into and/or out of the anti-torque device 10", resulting in a device similar to that shown in FIG. 2.

The anti-torque device 10" may include a handle 34" that defines a longitudinal axis that preferably extends generally perpendicularly from a longitudinal axis 15" defined by an elongated and generally hollow member 36". The handle 34" is not a necessary component and is merely provided in the instance of replacing the power tool with a hand-actuated screwdriver or in providing an additional holding/carrying feature for the surgeon. A proximal end 10a" of the hollow member 36" preferably includes an eye 38" having an eccentrically-shaped interior surface. In the present embodiment, the interior surface of at least a portion of the eye 38" is octagonally-shaped and is sized to matingly receive at least a portion of the motor shaft 20", which also preferably includes an exterior surface that is octagonally-shaped.

In operation, the user initially inserts the distal end 14b" of the drive shaft 14" into the proximal end 10a" of the hollow member 36" of the anti-torque device 10" (see FIGS. 11 and 12). Next, the user slides the drive shaft 14" completely within the hollow member 36", such that the distal end 14" of the drive shaft 14" is generally adjacent to or surrounded by a distal end 10b" of the hollow member 36" of the anti-torque device 10" and such that at least a portion of the motor shaft 20" matingly engages the interior surface of the eye 38" (see FIG. 13). In this position, the proximal end 10a" is preferably rotatably fixedly attached to at least a portion of the torque-generating body 12", such as the motor shaft 20", but preferably is not axially fixed such that the drive shaft 14" may be removed from the hollow member 36".

Once power is supplied to the torque-generating body 12", the drive shaft 14" applies a locking torque on one of the locking cap (not shown in FIGS. 11-13) and the pedicle screw 16 and the anti-torque device 10" applies a generally equal and opposite reaction torque to at least one of the pedicle screw 16, locking cap, fixation rod (not shown in FIGS. 11-13) and clamp. As with the first and second embodiments, the above-identified structure of the third embodiment allows the user to accomplish proper tightening of the locking cap to the pedicle screw with only a single hand.

Figure 14:
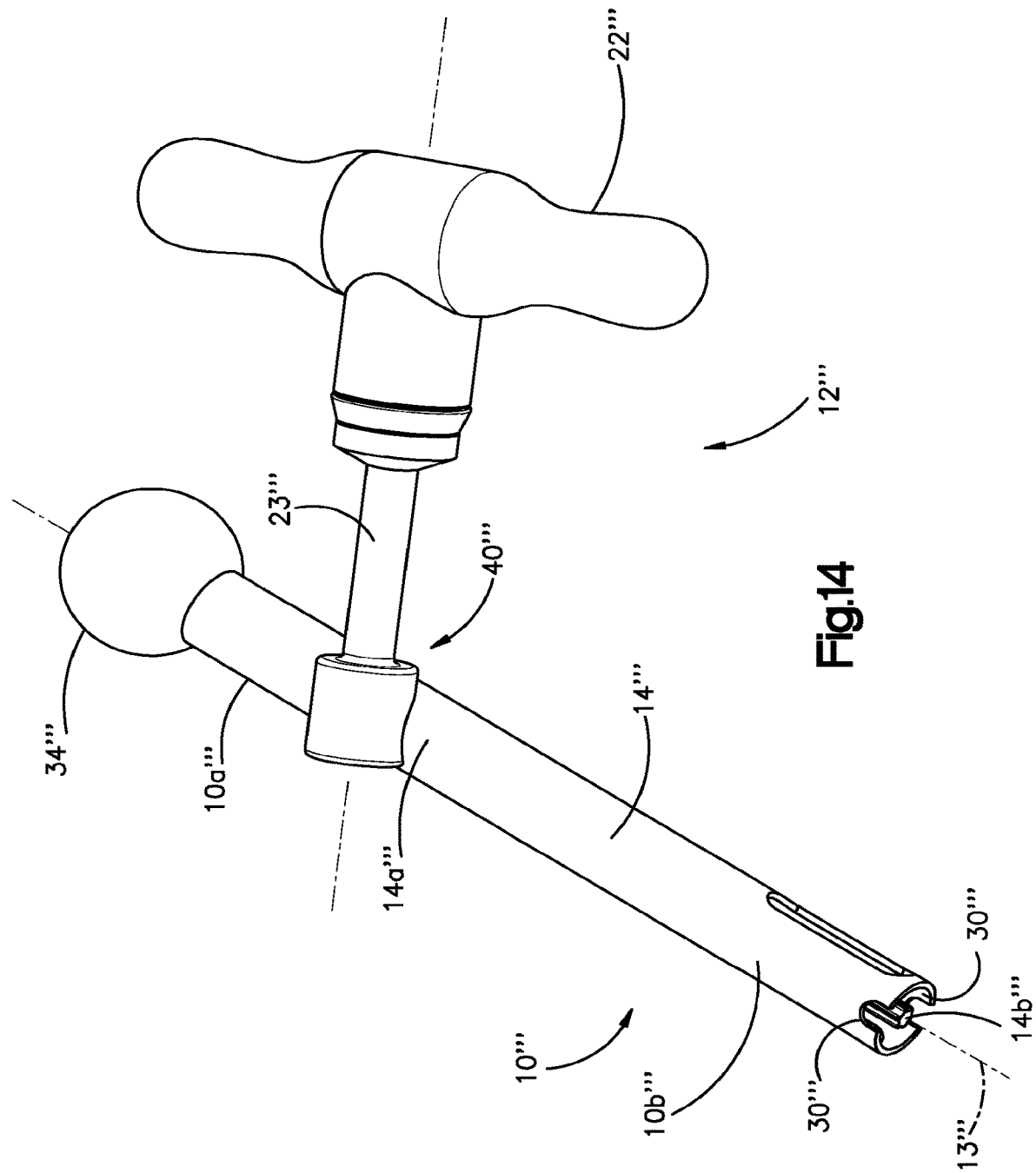
FIG. 14 is a perspective view of an anti-torque device in accordance with a fourth embodiment of the present invention, along with a hand-actuated screwdriver.

Referring to FIG. 14, a fourth embodiment of a combined anti-torque device and a torque-generating body, generally designated 10''' and 12''', respectively, is shown. Like numerals are utilized to identify like elements and three (3) prime symbols (''') are utilized to distinguish like components of the anti-torque device 10''' and torque-generating body 12''' of the fourth embodiment from those of the previous embodiments. The torque-generating body 12''' of the fourth embodiment is hand-actuated. Specifically, an input or T-shaped handle 22''' is operatively connected to a worm gear 40''' by a shaft. In operation, rotation of the T-shaped handle 22''' by a single hand of the surgeon rotates the shaft, which in turn rotates the worm gear 40''', which in turn rotates the drive shaft 14'''.

In the fourth embodiment, an input drive axis 23''', as defined by the shaft connecting the T-shaped handle 22''' to the worm gear 40''', is roughly perpendicular to a longitudinal axis 13''' of a drive shaft 14'''. Thus, all of the torque applied through the drive shaft 14''' is balanced by a distal end 10b''' of a hollow member 36''' of the anti-torque device 10''' and little or no net torque is applied to the pedicle screw. The anti-torque device 10''' of the present embodiment preferably includes archways 30''' and operates in a similar manner to the anti-torque device 10' of the second embodiment described above. The anti-torque device 10''' may include a handle 34''', which preferably extends generally perpendicularly from the shaft of the T-shaped handle 22''' and serves a similar purpose to the handle 34" of the third embodiment described above. In a variation of the forth embodiment, the worm gear arrangement is replaced by a set of bevel gears to accomplish the same effect of gear reduction while lowering the friction inherent in the use of bevel gears.

Figure 15:
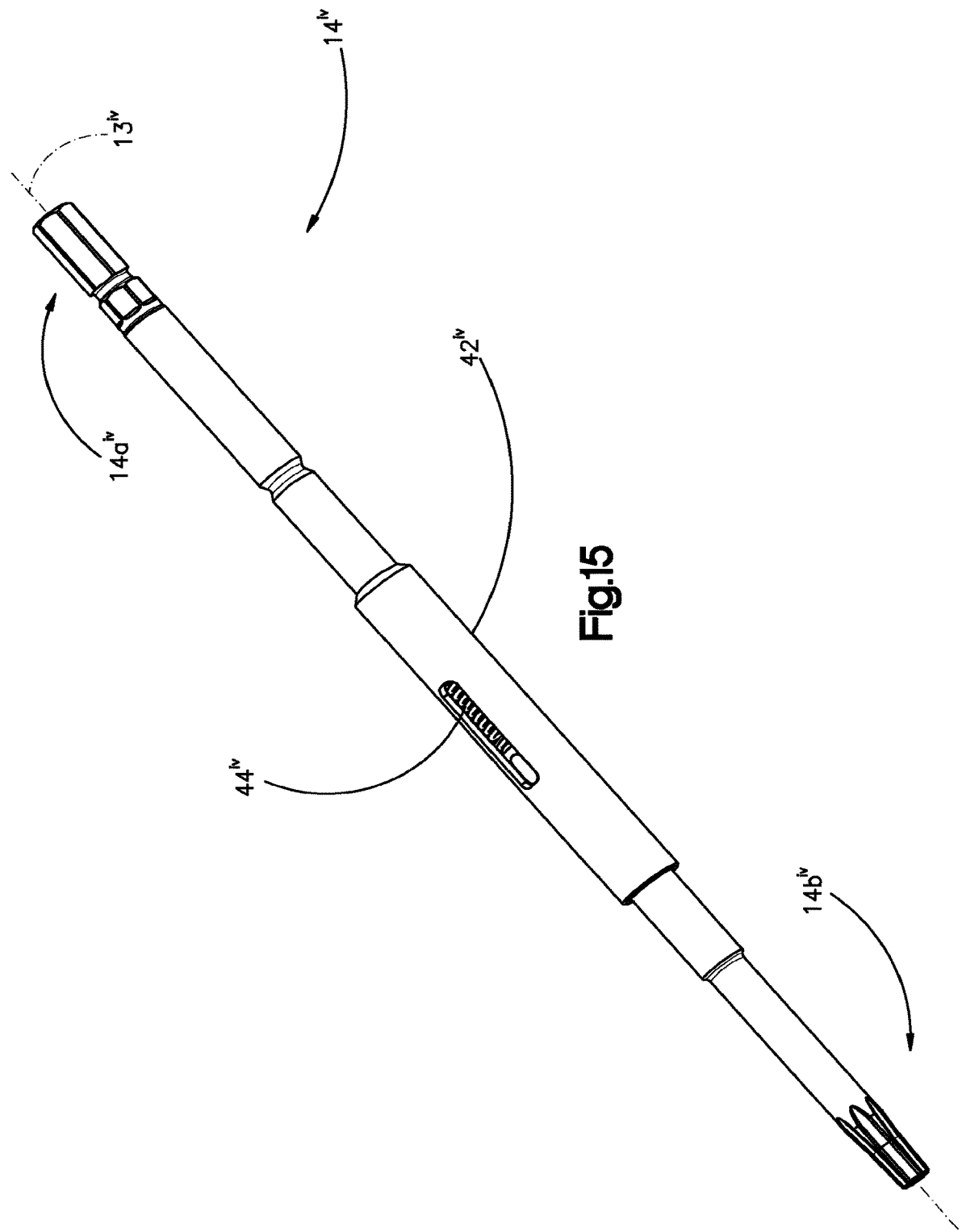
FIG. 15 is an alternative embodiment of a drive shaft for use with a hand-actuated screwdriver or a power tool.

Referring to FIG. 15, an alternative embodiment of a drive shaft, generally designated $14^{iv}$, is shown. The drive shaft $14^{iv}$ is adapted to be selectively used with either a hand-actuated screwdriver (not shown in FIG. 15) or a power tool (not shown in FIG. 5) and is adapted to be inserted into any one of the embodiments of the anti-torque device 10, 10', 10", 10''' described above. Like numerals are utilized to identify like components and a ($^{iv}$) symbol is utilized to distinguish like components of the drive shaft $14^{iv}$ of the present embodiment from those of the previous embodiments. The drive shaft $14^{iv}$ preferably includes an outer sleeve $42^{iv}$ that encloses a spring $44^{iv}$ (i.e., a spring-loaded sleeve or shaft). The outer sleeve $42^{iv}$ is selectively movable such that the distal end $14b^{iv}$ of the drive shaft $14^{iv}$ may be moved backwards approximately 10 mm against the spring $44^{iv}$ so that the anti-torque device may engaged while the distal end $14b^{iv}$ is pushed against the locking cap.

In operation, as a distal end $14^{iv}$ of the drive shaft $14^{iv}$ is engaged with one of a pedicle screw (not shown in FIG. 15) and locking cap (not shown in FIG. 15), the outer sleeve $42^{iv}$ quickly advances or moves downwardly and becomes rotatably fixed with one of the pedicle screw and locking cap. The design of the present embodiment reduces any risk of stripping the pedicle screw recess by turning the drive shaft while the distal end $14^{iv}$ of the drive shaft $14^{iv}$ advances to the pedicle screw.

Referring to FIGS. 16-19, a fifth embodiment of a combined anti-torque device and a torque-generating body, generally designated $10^v$ and $12^v$, respectively is shown. Like numerals are utilized to identify like elements and a prime symbol (') is utilized to distinguish like components of the anti-torque device $10^v$ and torque-generating body $12^v$ of the fifth embodiment from those of the other embodiments. The torque-generating body $12^v$ of the fifth embodiment is preferably hand-actuated. The torque-generating body $12^v$ may alternatively be a power driver. A proximal end of the torque-generating body $12^v$ includes an input handle 222 to allow the user to rotate the drive shaft $14^v$ with a single hand. The input handle 222 may include a torque limiting mechanism 224.

Figure 17:
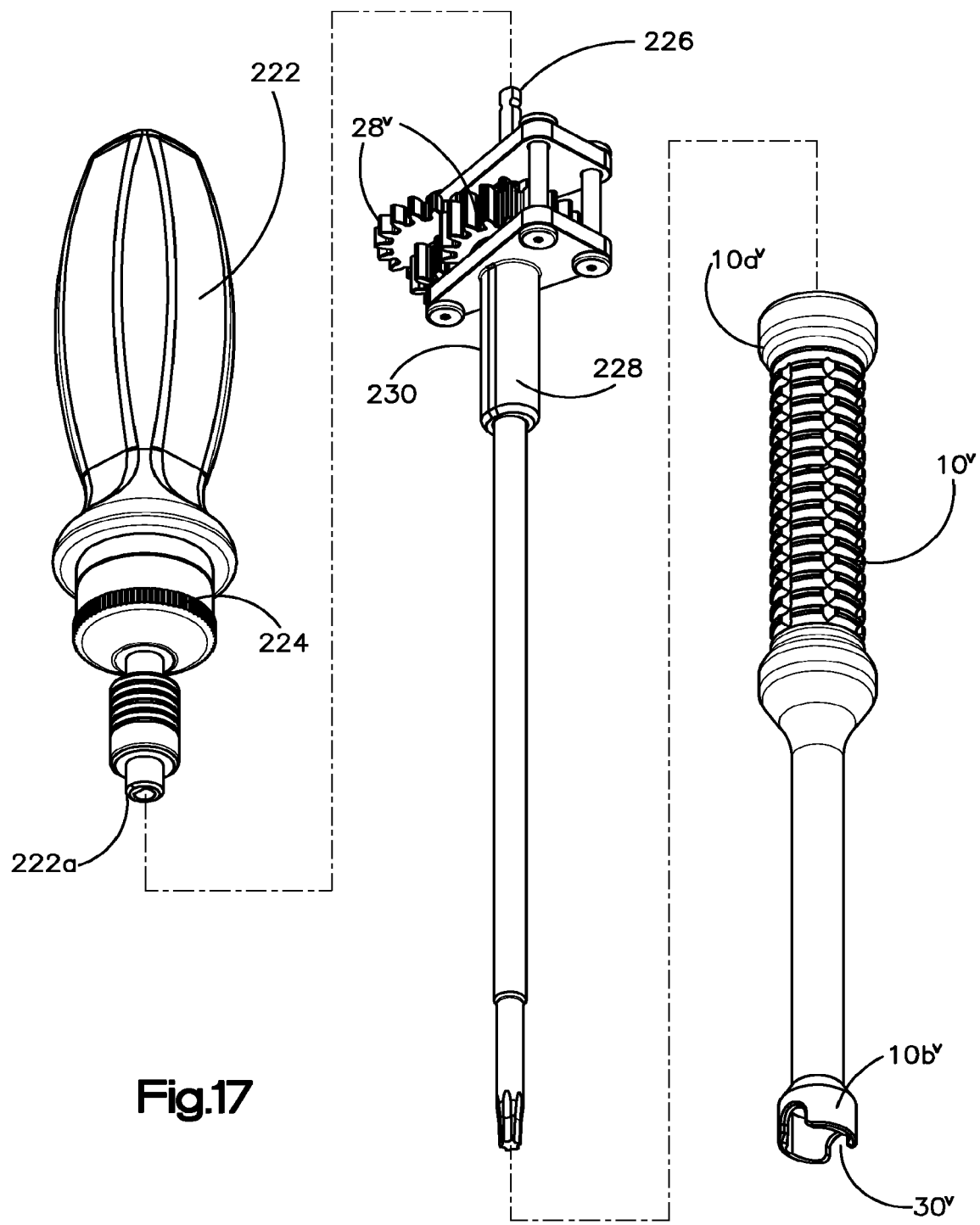
FIG. 17 is an exploded perspective view of the anti-torque device shown in FIG. 16.
Figure 18:
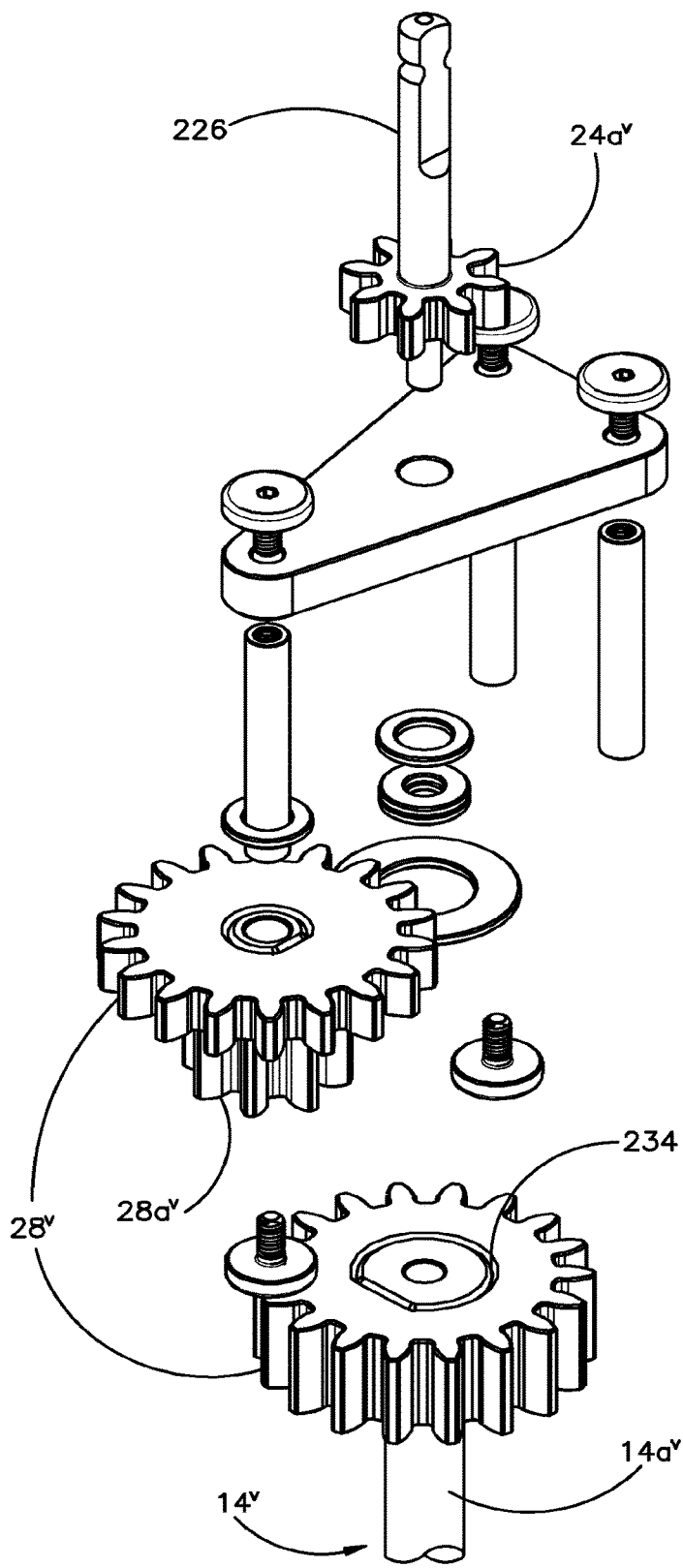
FIG. 18 is an exploded perspective view of a gearbox shown in FIG. 16.

In this embodiment, the distal end 222a of the input handle 222 engages a notched shaft 226 that is connected to a first gear $24a^v$ (FIG. 18). The rotation of the first gear $24a^v$ drives spur gears $28^v$ that are provided as a gearbox to reduce the required torque input and increase the torque output of the drive shaft $14^v$. The first spur gear $28^v$ preferably has a greater the number of gear teeth as the first gear $24a^v$. A spur $28a^v$ of the first spur gear $28^v$ operatively engages a second spur gear $28^v$. The gear tooth ratios of the spur $28a^v$ and spur gears $28^v$ may be as described above with regard to the second embodiment. In some implementations, the gear ratio of the gearbox maybe 5-to-1, with a range between 2-to-1 and 10-to-1. As such, for example, an input torque of 2½ Nm would result in an output torque on the drive shaft $14^v$ of 10 Nm after friction losses. In some implementations, the torque limiting mechanism 224 shown in FIGS. 16-17 may be provided in combination with either the notched shaft 226 or the drive shaft $14^v$.

As shown in FIGS. 16-19, the proximal end $14a^v$ of the drive shaft $14^v$ is operatively engaged with the second spur gear $28^v$. In an embodiment, at least a portion of the proximal end $14a^v$ of the drive shaft $14^v$ extends through at least a central portion of the second spur gear $28^v$ and is operatively connected thereto by a keyed opening 234 in the second spur gear $28^v$, such that rotation of the second spur gear $28^v$ directly rotates the drive shaft $14^v$. Thus, rotation of the first gear $24a^v$ by or through the torque limiting mechanism 224 rotates the drive shaft $14^v$ and increase the torque applied by the surgeon.

Figure 16:
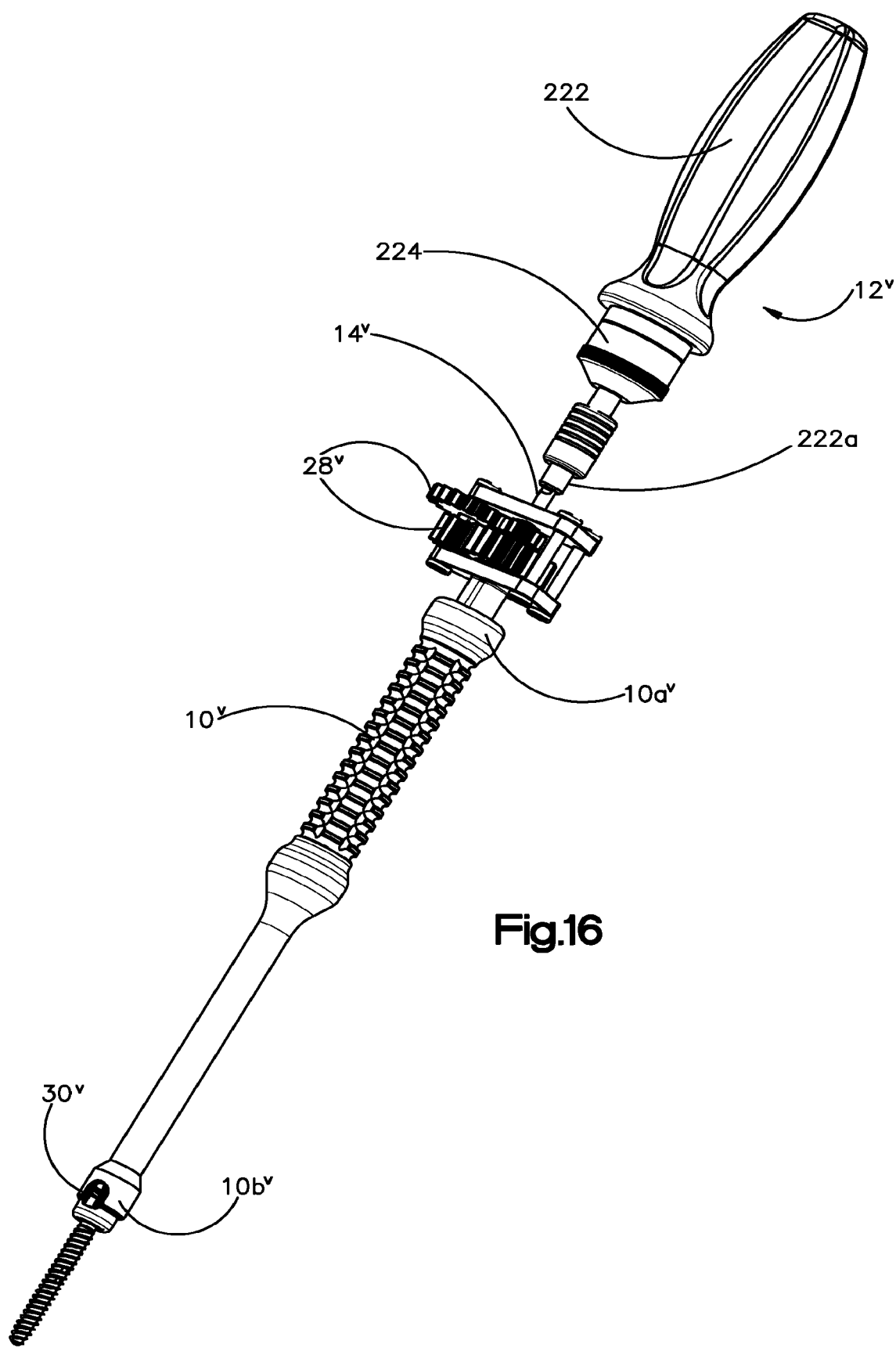
FIG. 16 is an elevation view of an anti-torque device in accordance with a fifth embodiment of the present invention.
Figure 19:
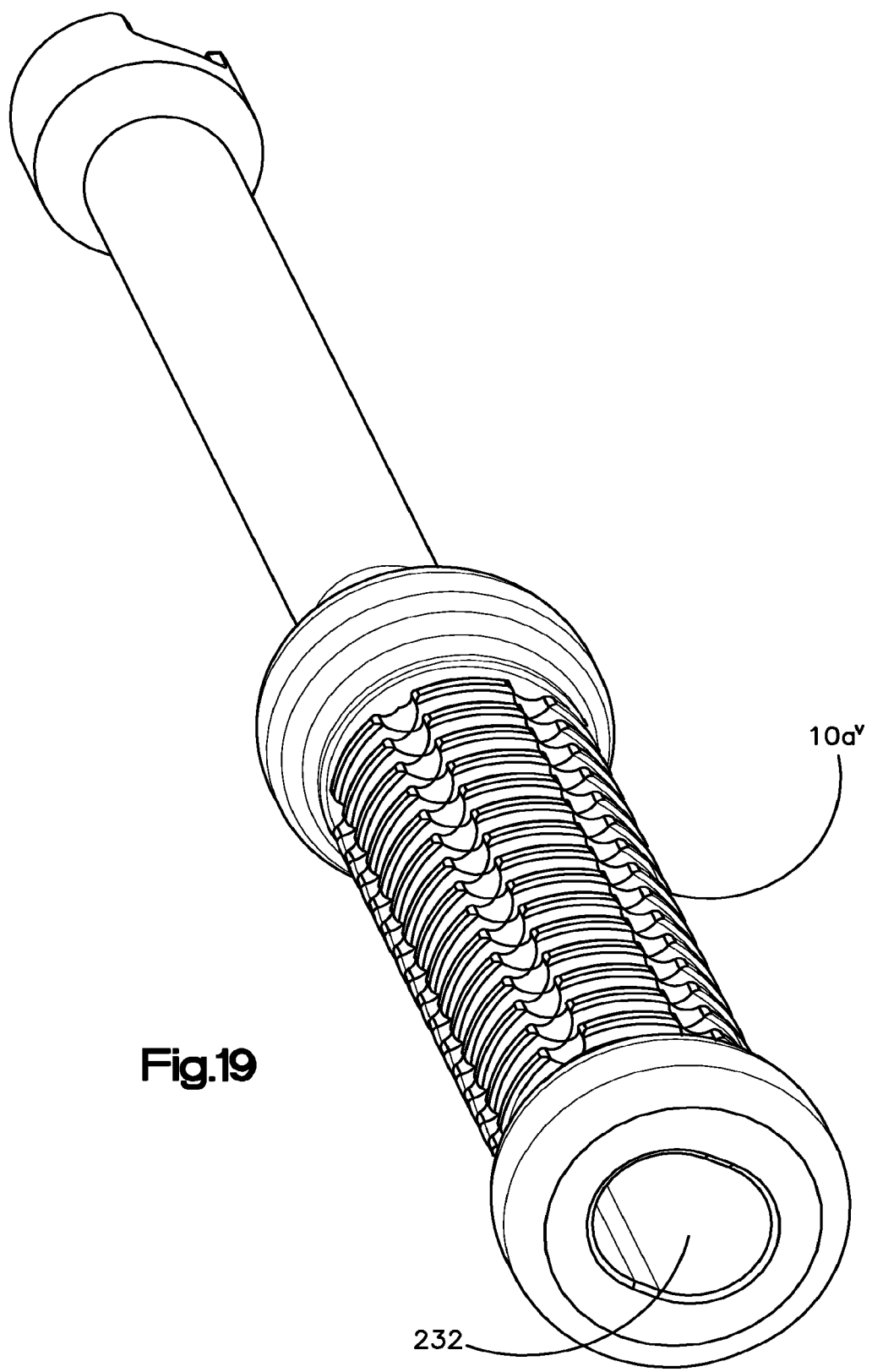
FIG. 19 is a perspective view of a proximal portion of the anti-torque device shown in FIG. 16.

A proximal end $10a^v$ of the anti-torque device $10^v$ is slidably attached to a portion of the torque-generating body $12^v$. As such, the anti-torque device $10^v$ may slide in the longitudinal direction for engagement, but is not able to rotate about the torque-generating body $12^v$. The proximal end $10a^v$ may be provided with a grip pattern, as shown in FIGS. 16 and 19, to reduce the likelihood of slippage during use. As shown in FIG. 19, the proximal end of the anti-torque device $10a^v$ is provided with a keyed interface 232 that engages a receiving face 230 of an end member 228 of the torque-generating body $12^v$ (see, FIG. 17). A distal end $10b^v$ of the anti-torque device $10^v$ preferably rotatably fixedly attaches to one of a pedicle screw 16, fixation rod 17 and that is part of the internal fixation system.

In operation, rotation of the handle 222 rotates the drive shaft $14^v$ with respect to the anti-torque device $10^v$. Thus, the drive shaft $14^v$ applies a locking torque on one of the locking cap 18 and the pedicle screw 16. Meanwhile the anti-torque device $10^v$, as fixed by the cooperation of the keyed interface 232 and the face 230, prevents the pedicle screw 16 from rotating and, thus, a generally equal and opposite reaction torque is applied to at least one of the pedicle screw 16, locking cap 18, fixation rod 17. The above-identified structure of the fifth embodiment allows the user to accomplish proper tightening of the locking cap 18 to the pedicle screw 16 with only a single hand.

As seen in FIGS. 16-17, the distal end $10b^v$ of the anti-torque device $10^v$ preferably includes at least one but preferably four (4) generally equally, radially spaced-apart archways $30^v$ that extend radially inwardly from the distal end $10b^v$. The archways $30^v$ provide clearance for at least a portion of the fixation rod 17 during operation of the anti-torque device $10^v$ and the torque-generating body $12^v$. In operation, at least a portion of one of the archways $30^v$ preferably contacts or engages at least a portion of the fixation rod 17 to generally hold the distal end $10b^v$ of the anti-torque device $10^v$ stationary.

It will be appreciated by those skilled in the art that changes could be made to the embodiments described above without departing from the broad inventive concept thereof. For example, the embodiments shown typically engage pedicle screws, nuts and/or rods used in the thoracic and lumbar spine. However, other applications in the spine may include pedicle screws, nuts and/or rods used in the cervical spine, pedicle hooks used in the cervical, thoracic or lumbar spine, plates or fixation rods used in anterior or lateral fixation of the spine, a vertical expandable rib, transconnectors as used as part of a spine rod construct, transverse bars as used as part of a spine rod construct, rod-to-rod connectors as used as part of a spine rod construct, and setscrews used in holding an end position in distractable devices such as vertebral interbody spacers and interspinous process spacers. Further, other applications may be tightening of locking screws or nuts used in bone fixation in various regions of the human body. It is understood, therefore, that this invention is not limited to the particular embodiments disclosed, but it is intended to cover modifications within the spirit and scope of the present invention as defined by the present disclosure.

We claim:

1. A system for tightening a locking cap onto at least a portion of a pedicle screw during spinal surgery, the system comprising:
a torque-generating body having a proximal end and an opposing distal end and defining a longitudinal axis extending therebetween, the distal end coupled to a handle;
a drive shaft rotatably driven by the torque-generating body, the drive shaft having a proximal end, an opposing distal end and a longitudinal axis extending therebetween, the proximal end of the drive shaft being operatively engaged to the distal end of the torque-generating body, the opposing distal end of the drive shaft engaging at least a portion of one of a locking cap and the pedicle screw, wherein rotation of said handle about the longitudinal axis of the drive shaft causes the drive shaft to rotate;

a gearbox operatively coupled to the torque-generating body and the drive shaft;

an anti-torque device comprised of an elongated and generally hollow member, the anti-torque device having a proximal end and an opposing distal end, the proximal end of the anti-torque device being fixed from rotating relative to at least a portion of the torque-generating body; and an end member provided at a distal end of the gearbox, the end member having a non-circular curvilinear shape in cross section including at least one generally planar surface, where the drive shaft is rotatably received within a central opening of the end member, wherein the proximal end of the anti-torque device comprises a longitudinally extending keyed interface which is slidably engaged to a corresponding longitudinally extending receiving face provided on the planar surface of the end member, wherein neither the end member nor the anti-torque device include a threaded engagement feature such that engagement between an outer surface of the end member and the longitudinally extending keyed interface of the anti-torque device couples the end member to the anti-torque device and fixes the end member from rotating relative to the anti-torque device.

2. The system of claim 1, wherein the distal end of the anti-torque device is fixed from rotating relative to at least a portion of one of the pedicle screw and a fixation rod.

3. The system of claim 1, wherein the anti-torque device and torque-generating body cooperate to create a generally balanced reaction between a locking torque $T_L$ generated by the torque-generating body and an opposite reaction torque TR generated by the anti-torque device.

4. The system of claim 3, wherein the torque $T_L$ generated by the torque-generating body is provided to one of the locking cap and the pedicle screw, and the opposite reaction torque $T_R$ generated by the anti-torque device is provided to one of the locking cap, the pedicle screw and a fixation rod.

5. The system of claim 1, wherein the torque-generating body is one of a motorized power tool, a pressurized fluid or a hand-actuated screwdriver.

6. The system of claim 1, wherein the anti-torque device is removably attached to the torque-generating body.

7. The system of claim 1, wherein the anti-torque device comprises an opening formed on a side wall proximate a connection point between the distal end of the drive shaft and at least a portion of one of a locking cap and the pedicle screw, wherein the anti-torque device comprises radially spaced-apart archways that extend radially inwardly from the distal end of the anti-torque device, the archways radially spaced-apart from the opening.

8. The system of claim 7, wherein a portion of one of the archways engages at least a portion of a fixation rod to maintain the distal end of the anti-torque device stationary.

9. The system of claim 1, wherein an interior surface of the distal end of the anti-torque device includes at least one of a recess and a protrusion sized and configured to engage the portion of the one of the locking cap, the pedicle screw and the fixation rod.

10. The system of claim 1, wherein the gearbox receives input torque from the torque-generating body and increases output torque of the drive shaft.

11. The system of claim 1, wherein the gearbox comprises a first gear operatively coupled to the distal end of the torque-generating body, and a first spur gear that operatively engages the first gear, wherein the first spur gear has a greater number of gear teeth than a number of gear teeth of the first gear.

12. The system of claim 11, wherein the first spur gear has twice the number of gear teeth as the first gear.

13. The system of claim 11, wherein the gear box further comprises a second spur gear, wherein a spur of the first spur gear operatively engages the second spur gear, wherein the second spur gear has a greater number of gear teeth then a number of gear teeth of the spur.

14. The system of claim 13, wherein the second spur gear has twice the number of gear teeth as the spur of the first spur gear.

15. The method of claim 13, wherein a proximal end of the drive shaft is operatively engaged with the second spur gear.

16. The method of claim 15, wherein at least a portion of the proximal end of the drive shaft extends through at least a central portion of the second spur gear and is fixedly connected thereto.

17. The system of claim 1, wherein the keyed interface of the anti-torque device is provided on a surface of a central opening extending through the anti-torque device, wherein the central opening of the anti-torque device has a non-circular shape in cross-section corresponding to the cross-sectional shape of the end member and including at least one generally planar surface, wherein the keyed interface of the anti-torque device is provided the planar surface of the central opening.

18. The system of claim 17, wherein the end member is slidably received within the central opening of the anti-torque device.

* * * * *

UNITED STATES PATENT AND TRADEMARK OFFICE
CERTIFICATE OF CORRECTION

PATENT NO. : 11,660,129 B2
APPLICATION NO. : 15/788149
DATED : May 30, 2023
INVENTOR(S) : Jason Yim et al.

It is certified that error appears in the above-identified patent and that said Letters Patent is hereby corrected as shown below:

In the Claims

In Column 13, Line 37 of Claim 3, the text, "TR" should read --$T_R$--

In Column 14, Line 28 of Claim 13, the text "then" should read --than--

Signed and Sealed this
Thirtieth Day of July, 2024

Katherine Kelly Vidal
*Director of the United States Patent and Trademark Office*